(12) United States Patent
Laskin et al.

(10) Patent No.: US 9,512,068 B2
(45) Date of Patent: Dec. 6, 2016

(54) AUGMENTING MOIETIES FOR ANTI-INFLAMMATORY COMPOUNDS

(71) Applicants: Rutgers, The State University of New Jersey, New Brunswick, NJ (US); Lehigh University, Bethlehem, PA (US)

(72) Inventors: Jeffrey D. Laskin, Piscataway, NJ (US); Ned D. Heindel, Easton, PA (US); Diane E. Heck, Rumson, NJ (US); Carl Jeffrey Lacey, Schnecksville, PA (US); Sherri C. Young, Clinton, NJ (US)

(73) Assignees: RUTGERS, THE STATE UNIVERSITY OF NEW JERSEY, New Brunswick, NJ (US); LEHIGH UNIVERSITY, Bethlehem, PA (US)

( * ) Notice: Subject to any disclaimer, the term of this patent is extended or adjusted under 35 U.S.C. 154(b) by 0 days.

(21) Appl. No.: 14/776,857

(22) PCT Filed: Mar. 14, 2014

(86) PCT No.: PCT/US2014/028329
§ 371 (c)(1),
(2) Date: Sep. 15, 2015

(87) PCT Pub. No.: WO2014/144073
PCT Pub. Date: Sep. 18, 2014

(65) Prior Publication Data
US 2016/0031804 A1    Feb. 4, 2016

Related U.S. Application Data

(60) Provisional application No. 61/790,870, filed on Mar. 15, 2013, provisional application No. 61/793,842, filed on Mar. 15, 2013.

(51) Int. Cl.

| | | |
|---|---|---|
| *C07C 261/00* | (2006.01) |
| *C07C 269/00* | (2006.01) |
| *C07C 271/00* | (2006.01) |
| *C07C 271/52* | (2006.01) |
| *A61K 47/48* | (2006.01) |
| *A61K 31/132* | (2006.01) |
| *A61K 31/198* | (2006.01) |
| *A61K 31/27* | (2006.01) |
| *A61K 31/4015* | (2006.01) |
| *A61K 31/405* | (2006.01) |
| *C07C 271/16* | (2006.01) |
| *C07C 271/22* | (2006.01) |
| *C07C 271/48* | (2006.01) |
| *C07D 207/16* | (2006.01) |
| *C07D 209/26* | (2006.01) |
| *C07C 271/12* | (2006.01) |
| *C07C 271/34* | (2006.01) |
| *C07C 271/50* | (2006.01) |

(52) U.S. Cl.
CPC .......... *C07C 271/52* (2013.01); *A61K 31/132* (2013.01); *A61K 31/198* (2013.01); *A61K 31/27* (2013.01); *A61K 31/405* (2013.01); *A61K 31/4015* (2013.01); *A61K 47/48038* (2013.01); *C07C 271/12* (2013.01); *C07C 271/16* (2013.01); *C07C 271/22* (2013.01); *C07C 271/34* (2013.01); *C07C 271/48* (2013.01); *C07C 271/50* (2013.01); *C07D 207/16* (2013.01); *C07D 209/26* (2013.01); *C07C 2101/16* (2013.01); *C07C 2102/42* (2013.01)

(58) Field of Classification Search
CPC ............ C07C 271/51; C07C 2101/16; C07C 2102/42; C07C 271/12; C07C 271/16; C07C 271/22; C07C 271/34; C07C 271/48; C07C 271/50; A61K 31/132; A61K 31/198; A61K 31/27; A61K 31/4015; A61K 31/405; A61K 47/48038; C07D 207/16; C07D 209/26
See application file for complete search history.

(56) References Cited

U.S. PATENT DOCUMENTS

| | | | |
|---|---|---|---|
| 2008/0107720 A1 | 5/2008 | Walters et al. | |
| 2009/0238905 A1 | 9/2009 | Gurney et al. | |
| 2011/0133121 A1* | 6/2011 | Shinohata | ............. C07C 263/04 252/182.12 |

OTHER PUBLICATIONS

Detoisien et al. (The Condensation of Lignin Model Compounds with Hexamethylene Diisocyanate British Polymer Journal, vol. 17, No. 3 1985).*
International Search Report and Written Opinion for International Application No. PCT/US2014/028329 dated Oct. 23, 2014.

* cited by examiner

*Primary Examiner* — Yevegeny Valenrod
*Assistant Examiner* — Blaine G Doletski
(74) *Attorney, Agent, or Firm* — Fox Rothschild LLP

(57) ABSTRACT

Augmented or synergized anti-inflammatory constructs are disclosed including terpenes covalently conjugated with other anti-inflammatory molecules such as nonsteroidal anti-inflammatory drugs, vanilloids, amino acids and polyamines; and anti-inflammatory molecules covalently conjugated with specific amino acids. For the latter, further conjugation with a choline bioisostere further augments the anti-inflammatory activity.

10 Claims, No Drawings

AUGMENTING MOIETIES FOR ANTI-INFLAMMATORY COMPOUNDS

CROSS-REFERENCE TO RELATED APPLICATIONS

This application is the U.S. National Phase of International patent application Ser. No. PCT/US14/28329, filed Mar. 14, 2014, which claims the benefit of priority under 35 U.S.C. 119(e) of U.S. Provisional Application No. 61/790,870, filed on Mar. 15, 2013, and of U.S. Provisional Application No. 61/793,842, filed on Mar. 15, 2013. The disclosures of which are incorporated herein by reference in their entireties.

STATEMENT REGARDING FEDERALLY SPONSORED RESEARCH OR DEVELOPMENT

This invention was made with government support under Grant No. U54AR055073 awarded by the National Institutes of Health. The government has certain rights in the invention.

FIELD OF THE INVENTION

The invention is directed to anti-inflammatory compounds which are synergistically enhanced in their anti-inflammatory activity through conjugation with specific amino acids and/or with specific other anti-inflammatory components. Also disclosed are methods of increasing the activity of an anti-inflammatory compound, which involve conjugating the anti-inflammatory compound with an amino acid and optionally further conjugating with a choline bioisostere, or conjugating one, two or more anti-inflammatory compounds with each other, for example, terpene, amino acid, vanilloid, or polyamine.

BACKGROUND OF THE INVENTION

The term "anti-inflammatory" refers to the property of a compound that reduces inflammation. Anti-inflammatory drugs make up about half of analgesics, remedying pain by reducing inflammation.

Nonsteroidal anti-inflammatory drugs (NSAIDs) are a class of drugs that provide analgesic and antipyretic (fever-reducing) effects, and, in higher doses, anti-inflammatory effects. The term "nonsteroidal" distinguishes these drugs from steroids, which, among a broad range of other effects, have a similar eicosanoid-depressing, anti-inflammatory action. As analgesics, NSAIDs are unusual in that they are non-narcotic. The most prominent members of the NSAID group of drugs are aspirin, ibuprofen and naproxen.

The widespread use of NSAIDs has meant that the adverse effects of these drugs are well known and have become increasingly prevalent as the population ages. The two main adverse drug reactions (ADRs) associated with NSAID use are gastrointestinal (GI) and renal effects. These effects are dose-dependent and, in many cases, severe enough to pose the risk of ulcer perforation, upper gastrointestinal bleeding, and death, thereby limiting the use of NSAID therapy. An estimated 10-20% of NSAID patients experience dyspepsia, and NSAID-associated upper GI adverse events are estimated to result in 103,000 hospitalizations and 16,500 deaths per year in the United States and represent 43% of drug-related emergency visits. Thus, the clinical problems with NSAIDs and the need for replacement anti-inflammatories are well recognized.

For at least these reasons, it would be desirable to find substitutes for the current NSAIDs having increased anti-inflammatory potency and a higher safety margin.

BRIEF SUMMARY OF THE INVENTION

It has now been discovered that one solution to this problem is to improve the potency and safety of anti-inflammatory compounds through the covalent combination of component anti-inflammatory moieties and/or conjugation with a specific amino acid, optionally with further conjugation with a choline bioisostere.

Aspect I

Terpenes, amino acids, aliphatic polyamines such as spermine and spermidine, and vanilloid platforms (e.g., 4-hydroxy-3-methoxybenzyl amine, commonly called vanillylamine; 4-hydroxy-3-methoxybenzyl alcohol, commonly called vanillyl alcohol; zingerone; [6]-paradol; and eugenol), are known to display modest anti-inflammatory and antinociceptive activity in animal and cellular models. In addition, aliphatic and alicyclic carbamates are known to be inhibitors of fatty acid amide hydrolase (FAAH), an enzyme whose inhibition is linked to anti-inflammatory effects. Thus, the individual components of the anti-inflammatory constructs of a first aspect of the invention, and the bonds that link them all together, provide a therapeutic benefit that can be greater than the sum of the parts.

It has now been discovered that the double and triple combinations of these anti-inflammatory components covalently linked together with at least one carbamate bond yields an augmented anti-inflammatory molecule whose net activity exceeds that of its individual building blocks. Some of these assemblies exceed the anti-inflammatory effects of the traditional NSAIDs.

The specific structural assemblies claimed herein include:

| | |
|---|---|
| terpene-vanilloid | Formula 1 |
| vanilloid-polyamine-vanilloid | Formula 2 |
| vanilloid-amino acid-terpene | Formula 3 |
| terpene-polyamine-terpene | Formula 4 |
| vanilloid-amino acid-vanilloid | Formula 5 |
| terpene-amino acid-terpene | Formula 6 |
| terpene-amino acid-vanilloid | Formula 7 |

In one embodiment, the carbamate-linked structures have the following general structures:

| | |
|---|---|
| terpene-(carbamate)-vanilloid | Formula 1A |
| vanilloid-(carbamate)-polyamine-(carbamate)-vanilloid | Formula 2A |
| vanilloid-(carbamate)-amino acid-(ester)-terpene | Formula 3A |
| terpene-(carbamate)-polyamine-(carbamate)-terpene | Formula 4A |
| vanilloid-(carbamate)-amino acid-(amide)-vanilloid | Formula 5A |
| terpene-(carbamate)-amino acid-(ester-terpene | Formula 6A |
| terpene-carbamate)-amino acid-(amide)-vanilloid | Formula 7A |

Specific examples of the components usable in construction of Formulae 1 to 7 and 1A to 7A anti-inflammatory conjugates include the following.

For terpenes: The terpene of the synergistic anti-inflammatory drug conjugate is selected from the group consisting of thymol, carvacrol, menthol, geraniol, nerol, farnesol, myrtenol, cumyl alcohol, citronellol, borneol, linalool, alpha-terpineol, and perillyl alcohol. If the drug construct contains more than one terpene molecule, they may be different or the same.

For vanilloids: The vanilloid moiety of the synergistic anti-inflammatory drug conjugate is selected from the group consisting of 4-hydroxy-3-methoxybenzyl amine commonly called vanillylamine, 4-hydroxy-3-methoxybenzyl alcohol commonly called vanillyl alcohol, zingerone, [6]-paradol, and eugenol. If the drug construct contains more than one vanilloid molecule, they may be different or the same.

For polyamines: The polyamine anti-inflammatory component is selected from the group consisting of spermidine, spermine and putrescine.

For amino acids: The amino acid anti-inflammatory moiety is selected from valine, leucine, isoleucine, glycine, cysteine, phenylalanine, norvaline, and other suitable amino acids known to possess anti-inflammatory activity. The amino acids can be chiral or racemic. The chirality of the chiral amino acids can be L- or R- depending on the desired activity and release profile.

Aspect II

A second aspect of the present invention is directed to the surprising discovery that conjugation of certain anti-inflammatory moieties, especially NSAIDs, vanilloids, and ketone bodies, with selected amino acids, and optionally further conjugated with a choline bioisostere, synergistically increases the anti-inflammatory activity of the conjugate, when compared to the anti-inflammatory drug itself.

Thus, one embodiment of the present invention is directed to a synergistic anti-inflammatory drug-amino acid conjugate, comprising (a) at least one anti-inflammatory compound, and (b) at least one amino acid covalently linked to the anti-inflammatory compound, where the anti-inflammatory activity of the conjugate is greater than the activity of the anti-inflammatory compound alone. The synergistic anti-inflammatory drug-amino acid conjugate can further incorporate a choline bioisostere (e.g., the 3,3-dimethylbutyl moiety, —OCH$_2$CH$_2$C(CH$_3$)$_3$, or it's silicon analog, —OCH$_2$CH$_2$Si(CH$_3$)$_3$), preferably as the ester, so that another embodiment of the present invention is directed to a synergistic anti-inflammatory drug-amino acid-choline bioisostere conjugate, comprising (a) the anti-inflammatory drug-amino acid conjugate above, and (b) a choline bioisosteric ester, covalently linked to the amino acid carboxyl of said anti-inflammatory drug-amino acid conjugate.

In one embodiment the amino acid is covalently linked to the platform therapeutic agent through an amino or carboxyl group as either an amide or an ester moiety.

In one embodiment the amino acid of the synergistic anti-inflammatory drug-amino acid conjugate is selected from the group consisting of valine, nor-valine, leucine, iso-leucine, glycine, cysteine, proline and phenylalanine.

In one embodiment the anti-inflammatory compound is selected from the group consisting of non-steroidal anti-inflammatory drugs (NSAIDs), vanilloids, and ketone bodies. In a particular embodiment, the NSAID is selected from the group consisting of diclofenac, ibuprofen, naproxen, and indomethacin. The vanilloid is selected from vanillyl alcohol, phenolic hydroxyl-protected vanillyl alcohol (3-methoxy-4-acetyloxybenzyl alcohol), and vanillylamine. The ketone body is selected from 3-hydroxybutyrate or a homologue thereof. Vanillyl alcohol and vanillylamine are both known to possess anti-inflammatory properties. So-called "ketone bodies" of which 3-hydroxybutyric acid is a prime example, have been increasingly recognized as possessing anti-inflammatory properties.

In one embodiment, the synergistic anti-inflammatory drug-amino acid conjugate has the structure of Formula (I):

AI-NH—CHR—C(=O)O-Q$^1$    Formula (I)

where AI represents an anti-inflammatory drug moiety such as an NSAID-CO—, a vanillyl moiety, or 3-hydroxybutyryl, where R is selected from the group consisting of hydrogen, optionally substituted alkyl, optionally substituted cycloalkyl, optionally substituted aryl, and optionally substituted heteroaryl, and where Q$^1$ can be selected from hydrogen, alkyl or heteroalkyl. In one specific embodiment, Q$^1$=—CH$_2$CH$_2$C(CH$_3$)$_3$. Examples of this embodiment include NDH 4476, 4535, 4537, 4572, 4576, 4577, 4578, 4591, 4595, 4596, 4613, 4614, 4615, 4617, 4618, 4619, 4627, 4628, 4651, 4652, 4653, and 4654 as referenced herein.

In another embodiment, the synergistic anti-inflammatory drug-amino acid conjugate has the structure of Formula (II):

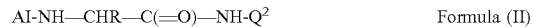

AI-NH—CHR—C(=O)—NH-Q$^2$    Formula (II)

where AI represents an anti-inflammatory moiety (viz., NSAID-CO—, vanillyl alcohol-CO—, and such ketone bodies as 3-hydroxybutyryl); R is selected from the group consisting of hydrogen, optionally substituted alkyl, optionally substituted cycloalkyl, optionally substituted aryl, and optionally substituted heteroaryl; Q$^2$ is selected from hydrogen or the vanillyl moiety (i.e., 3-methoxy-4-hydroxybenzyl), —CH$_2$CH$_2$C(CH$_3$)$_3$ or —CH$_2$CH$_2$Si(CH$_3$)$_3$. If vanillylamine (i.e., 3-methoxy-4-hydroxybenzyl-NH—) is attached to any of these anti-inflammatory amino acid platforms it constitutes a shelf-stable, slowly metabolized moiety. However, if vanillyl alcohol (i.e., 3-methoxy-4-hydroxybenzyl-O—) is attached, the resulting candidate pharmaceuticals are unstable unless the free-phenolic hydroxyl is protected by acylation. Acetate is a preferred protecting group and the derived products are suitable therapeutic candidates. Examples of this embodiment include NDH 4479, 4483, and 4571 as referenced herein.

DETAILED DESCRIPTION OF THE INVENTION

Aspect I

Surprisingly, it has now been discovered that weak anti-inflammatory moieties can be covalently linked by carbamate bonds to yield conjugate constructs of enhanced potency for suppression of inflammation.

One aspect of the present invention is directed to an anti-inflammatory conjugate where the anti-inflammatory component comprises at least one compound selected from the group consisting of anti-inflammatory terpenes, anti-inflammatory vanilloids, anti-inflammatory polyamines and anti-inflammatory amino acids.

A related aspect of the invention is directed to a method of improving the potency of an anti-inflammatory compound by linking it to another anti-inflammatory compound via a carbamate linkage, where the potency of the conjugate is greater than the sum of its parts.

In one embodiment of the present invention the terpene, amino acid, vanilloid, or polyamine is not employed as a single component but as an augmenting component, covalently linked by a carbamate moiety to another anti-inflammatory moiety or to two other anti-inflammatory moieties, wherein they together serve to enhance or synergize performance. The conjugates may be bifunctional (meaning just two moieties) or tri-functional (meaning three components), or higher. In addition the carbamate linking bond itself can also convey anti-inflammatory activity to the conjugate.

Carbamate compounds are known to achieve anti-inflammation effect in vivo by inhibition of fatty acid amide hydrolase. In an inhibitory screen against fatty acid amide hydrolase (FAAH), the inventive carbamates were found to possess $IC_{50}$ values which ranged from 9 µM to 1 mM for inhibition of FAAH. Some molecules were too lipophilic to dissolve in the enzyme assay medium and hence could not be tested. While there was no direct linear correlation between the compound's efficacy as an FAAH inhibitor and its potency in suppressing inflammation, many of the best inflammation suppressants were also FAAH inhibitors. The FAAH $IC_{50}$ values are noted with the compound examples.

Hydrolysis of the conjugates can release the terpene and any other co-anti-inflammatories to affect the therapeutic benefit in vivo. Unfortunately, in several cases hydrolysis was too fast (of the order of minutes) to make the compounds practical as pharmaceuticals and stabilization of the conjugate had to be addressed.

For example, as exemplified by the structures NDH4481, 4483, and 4485, if one attempts the incorporation into a conjugate of the vanilloid vanillyl alcohol (also known as 4-hydroxy-3-methoxybenzyl alcohol) through its benzyl alcohol component (the —CH$_2$OH), a conjugate is produced that is rapidly hydrolyzed. It is known that 4-hydroxy benzyl-X systems [e.g., p-HO—Ar—CH$_2$—X], wherein X is a good leaving group, can rapidly decompose via a quinone methide intermediate. Capping the phenolic hydroxyl with an acetate group solves the problem, and hydrolysis lifetimes of >2 hours are then observed. This problem is not observed with the vanillylamines when linked through their amino nitrogens; these are stable materials.

A second case of decomposition that is too rapid can be seen in NDH4590 and 4593. Even though these compounds have impressive anti-inflammatory effects in the Mouse Ear Vesicant Model (MEVM) assay, their half-lives in sera or in any polar aqueous medium are comparatively short (hours). We have discovered that this is because the nucleophilic internal secondary amine NH executes an intramolecular nucleophilic attack on the carbonyl of the carbanmate thereby freeing the terpene or the vanilloid component. This is a controllable, or tunable, chemically-induced hydrolysis that does not require an enzyme.

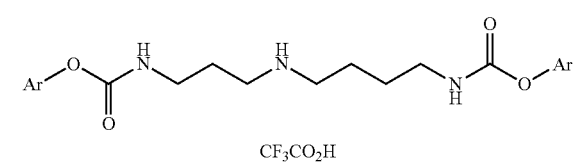

CF$_3$CO$_2$H
Ar = 1. terpene phenol: thymol or carvacrol
2. vanilloid: eugenol or zingerone

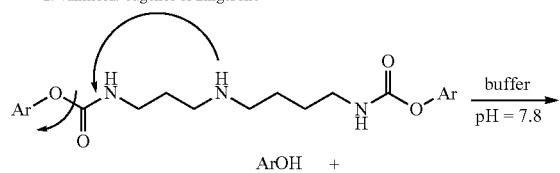

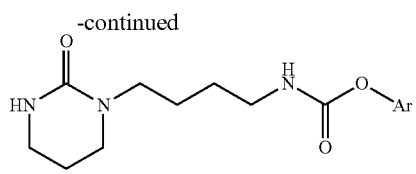

These compounds possess a terpene or vanilloid carbamate at both ends of the molecule in each case. With the unsymmetrical polyamine we have found that the cyclization occurs to form the six-membered ring only (versus a seven-membered ring).

Either making a salt (such as the trifluoroacetate, hydrochloride, mesylate, or other pharmaceutically acceptable salt) or a labile amide (for example, the trifluoroacetamide, trinitrobenzamide, or tris-trifluorobenzamide) on the internal NH solves the problem, and sufficiently long hydrolysis half-lives are then observed (days). The anti-inflammatory activity was unaffected by these stabilizing modifications, only the time of on-set of the effect was varied (cf. NDH4616, 4622, 4630, 4631, 4635, 4637 and 4649). Half-life for release can be controlled or tuned as noted above, by protonation or amide formation, but it can also be controlled by varying the nature of the anti-inflammatory leaving group. For example, zingerone is released much faster (half-life about 2 hours) than are carvacrol or thymol (half-lives about 2 days), which in turn are released much faster than an aliphatic terpene such as geraniol or borneol (marginal release after several days). The kinetics of release follow the typical organic moiety "leaving group" abilities.

Aspect II

Surprisingly, it has now been discovered that selected amino acids (for example valine, leucine, isoleucine, glycine, cysteine, phenylalanine, proline and norvaline) potentiate or synergize the activity of anti-inflammatory drugs when covalently attached to the parent drug molecules. When attached to known anti-inflammatory moieties, these amino acids augment, or synergize, the anti-inflammatory potency, provide a bio-compatible controlled-release, and permit adjustment of the pharmacologic properties of the parent anti-inflammatory drug.

Thus, in a second aspect of the invention, the amino acid can be used as a "capping" group on an anti-inflammatory such as a NSAID, a vanillyl alcohol or a vanillylamine. In one embodiment, the amino acid can be attached through its amino group to a carboxyl group in the platform anti-inflammatory molecule leaving a pendant carboxyl from the amino acid which can be free ($Q^1$=H) or can be esterified ($Q^1$=alkyl) for enhancement of properties or for ease of handling. A preferred alkyl group is a choline mimic, such as —CH$_2$CH$_2$C(CH$_3$)$_3$ or its silicon bioisostere, —CH$_2$CH$_2$Si(CH$_3$)$_3$. In one specific embodiment, constructs or scaffolds of this type can be characterized as shown in Formula (I):

AI-NH—CHR—C(=O)O-Q$^1$  Formula (I)

In a second embodiment, herein called Formula (II), when one anti-inflammatory compound contains an amino group, such as in the transient receptor potential cation channel subfamily V member 1 (TRPV1) inhibitor vanillylamine, the amino acid augmentation moiety can be linked via its carboxyl resulting in a pendant amino to which can be attached a second anti-inflammatory component such as an NSAID-CO—, a vanillyl alcohol-CO—, or a 3-hydroxybutyryl (3-HB) unit (as representative of a ketone body).

AI-NH—CHR—C(=O)—NH-Q$^2$  Formula (II)

NDH 4571 in which 3-HB is mounted on a valine platform linked to a vanilloid, displayed a 69% suppression of chloroethyl ethyl sulfide (CEES)-induced inflammation at the standard test dosage in the MEVM, considerably higher than any of the fragment pieces of that conjugate.

EXAMPLES

Materials and Methods

All reactants and solvents used were of the highest purity commercial grade and were employed without further purification. All amino acids used herein were the L-amino acids and were purchased from Sigma-Aldrich (Saint Louis, Mo.). The 2-(2-methoxynaphthalene-6-yl) propanoic acid (naproxen) used was the (S)-enantiomer. All other reagents were used as racemates, unless otherwise noted. All reactions were performed in oven-dried apparatus under a nitrogen atmosphere, unless otherwise noted.

All solvents used were anhydrous, unless otherwise noted. NMR spectra were recorded on a Bruker multinuclear spectrometer and chemical shifts are reported as ppm using tetramethylsilane (TMS) as an internal standard. $^1$H NMR spectra were recorded at 500 MHz, while $^{13}$C NMR spectra were recorded at 125 MHz. Elemental analyses were performed at Intertek (Whitehouse, N.J.). All thin layer chromatography (TLC) was performed on Analtech silica gel plates (250 microns).

Biological Evaluations

Ellman Assay

The modified Ellman assay for inhibition of acetylcholinesterase (AChE) and the mouse ear vesication assay (MEVA) have been described in detail by us (see S. C. Young et al, *J Appl Tox,* 2012, 32: 135-141). AChE (Type V-S from electrophorus electricus), acetylthiocholine iodide (ATChI), 5,5'-dithiobis(2-nitrobenzoic acid) (DTNB) and tacrine from EMD Chemicals (Gibbstown, N.J.). Cholinesterase inhibition was assayed spectrophotometrically at 412 nm according to Ellman's method. Assays were performed in polystyrene 96-well plates (Corning 96-well flat transparent) and a conventional micro-plate reader was employed for kinetic readings (Tecan Infinite 200 multimode). The following reagents were added to the wells: 200 μL of 0.5 mM DTNB in sodium phosphate buffer (100 mM, pH 8), 30 μL of inhibitor stock solution in methanol, 20 μL of 1.25 units/mL of AChE in sodium phosphate buffer (20 mM, pH 7), and 50 μL of 3 mM ATCh in buffer (100 mM, pH 8). Immediately after the substrate was added, the absorption signal was measured at 30 s intervals over 5 min at 25° C. Percentage inhibition was calculated relative to a negative control (methanol). The background signal was measured in control wells containing every reagent except for the substrate. $IC_{50}$ values were obtained from a minimum of eight concentrations in duplicate and by fitting the experimental data with a dose-response curve using Prism software (Version 5.00, GraphPad Software, San Diego, Calif.).

Mouse Ear Vesicant Model (MEVM)

Animal studies were approved by the Rutgers University Institutional Animal Care and Use Committee and received human care in compliance with the institution's guidelines, as outlined in the Guide for the Care and Use of Laboratory Animals of the National Academy of Sciences. Compounds were assessed as inhibitors of inflammation using the MEVM as previously described (Casillas, R P., et al., Therapeutic approaches to dermatotoxicity by sulfur mustard. 1.Modulaton of sulfur mustard-induced cutaneous injury in the mouse ear vesicant model, *J. Appl. Toxicol.,* 2000, 20, Suppl 1, S145-51), except that female CD-1 mice (4-6 weeks old) were used. Either CEES, chloroethyl ethyl sulfide (65 μmoles) or TPA, 12-O-tetradecanoylphorbol-13-acetate, (1.5 nmol) was used to induce inflammation. To evaluate each compound, ears (3-4 mice per group) were treated with 20 μL, of vehicle control (methylene chloride or acetone) or the test compound (1.5 μmol) in 20 μL, of the appropriate vehicle. After 5 h, mice were euthanized and ear punches (6 mm in diameter) were taken and weighed. Once the raw data were obtained, masses of ear punches were averaged and the percent reduction of vesicant-induced edema and inflammation was calculated using the method of Casillas et al. Raw data were analyzed using a one-way ANOVA to evaluate statistical significance ($P<0.05$).

Inflammation suppression, if observed, is of course dose related but is reported herein only at the standard dose mentioned above. On occasion, mostly with ibuprofen analogs, the vesicant-induced damage is augmented by the candidate anti-inflammatory and these substances are designated as irritants. Also, in some cases the anti-inflammatory candidate suppresses the mean weight of the ear punches from the test ears below that observed with the untreated control and these results are stated as >100% suppression.

Examples of Aspect I

The bifunctional and tri-functional conjugates of Aspect I of the invention were prepared and tested in a standard in vive MEVM assay for their efficacy compared to that of the parent terpene, amino acid, polyamine, or vanilloid from which each was assembled. Terpene inflammation suppression scores (average of TPA-induced and CEES-induced injuries) ranged from myrtenol (6%), thymol (14%), carvacrol (15%), cumyl alcohol (16%), geraniol (35%), menthol (38%). perillyl alcohol (43%), and farnesol (69%). All terpenes, except farnesol, had inflammation suppression scores less than 45%. The inflammation scores of typical vanilloids were similarly low and none exceeded 40%, e.g., vanillin (11%), vanillyl alcohol (31%), and vanillylamine (35%). In this assay inflammation suppression scores for the amino acids and the polyamines were under 30%. The traditional NSAIDs were under 40% in inflammation suppression scores, e.g., ibuprofen (−23%, an irritant % inflammation inducer), S-naproxen (31%), piroxicam (32%), diclofenac (37%), and indomethacin (39%).

The synergistic effects of combination of weakly potent anti-inflammatory components into conjugates are readily evident in the compounds of the invention. As an example of the Formula 1 class recited earlier herein, the terpene carvacrol by itself displayed inflammation suppression of 19% and 10% for CEES and TPA-induced inflammation respectively while its carbamate conjugate with vanillylamine (NDH4574) showed a significantly improved suppression of 89% and 88% (CEES and TPA).

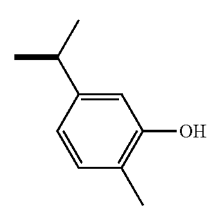

Carvacrol

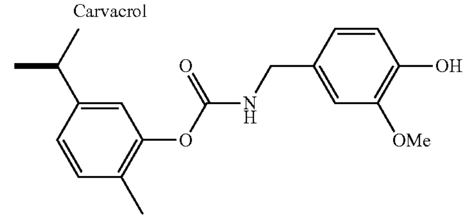

NDH4576

Another Formula 1 conjugate combines the terpene linalool to the vanilloid, vanillylamine, to yield the construct (NDH4624) which displayed a 92% suppression of CEES-induced inflammation.

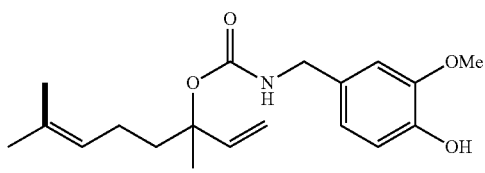

NDH4624

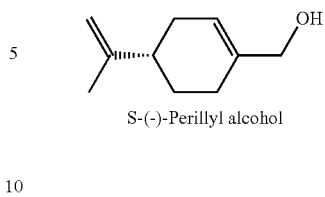

S-(-)-Perillyl alcohol

As another example of the Formula 1 conjugate, the terpene (geraniol) coupled to the vanilloid (vanillylamine) by a carbonate linkage and designated as NDH4484 had a 64% suppression (CEES-induced injury) and a 71 µM inhibition of fatty acid amide hydrolase (FAAH).

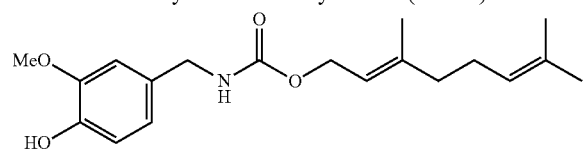

NDH4484

Similarly, a Formula 1 example involving perillyl alcohol showed the same trend with an inflammation suppression score of 43% (for the parent "free" terpene) while its carbamate conjugate with vanillylamine (NDH4498) showed an enhanced suppression of 53% (CEES) and 76% (TPA). This carbamate showed an $IC_{50}$ for inhibition of fatty acid amide hydrolase (FAAH) of 14 µM.

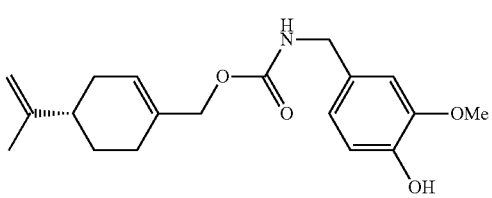

NDH4498

The Formula 2 conjugates (vanilloid-polyamine-vanilloid) can be illustrated by the construct of eugenol-spermidine-eugenol (NDH4635) which displays an inflammation suppression of 73% (CEES-induced inflammation) and zingerone-spermidine-zingerone

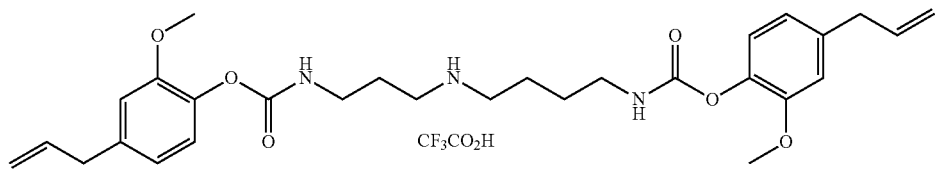

NDH4635

(NDH4637) which displays an 89% suppression against CEES-induced and 93% suppression against TPA-induced inflammation. The salt is needed to slow hydrolytic release of the zingerone.

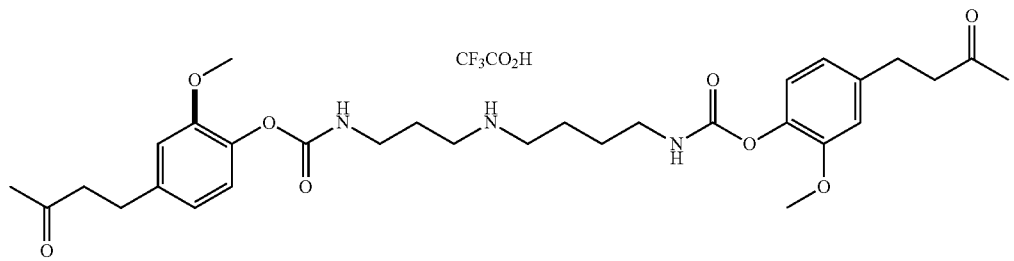

NDH4637

A tri-functional conjugate, NDH4486, (a Formula 3 example), in which the terpene geraniol (35% inflammation suppression score as unconjugated terpene molecule) was linked to the amino acid valine by a carbamate linkage and thence to the vanilloid vanillylamine, proved especially potent (91%) in suppression of TPA-induced inflammation in the mouse ear.

polyamines such as putrescine, spermidine, and spermine can display anti-inflammatory effects either as free molecular entities or as conjugates with all trans-retinoic acid. These effects are clearly augmented by attachment to terpenes through carbamate linkages.

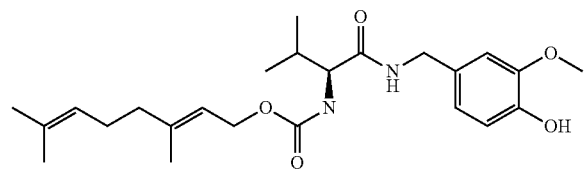

NDH4486

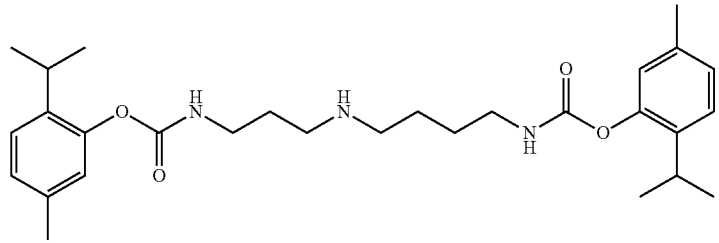

NDH4593

As an example of the Formula 4 conjugates, when carvacrol was linked as a bis-derivative to the well-known polyamine, spermidine. the inflammation suppression of the combined moiety increased to 71% against CEES-induced and 110% against TPA induced inflammatory injury (see NDH4593 shown below). The naturally occurring In addition, in a Formula 4 example, thymol displayed an inflammation suppression score of 14% while its carbamate conjugate with spermidine (NDH4590) showed an impressive and complete inflammation suppression of 100% against either CEES or TPA-induced injury.

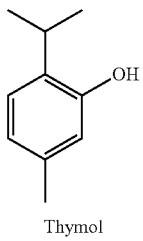

Thymol

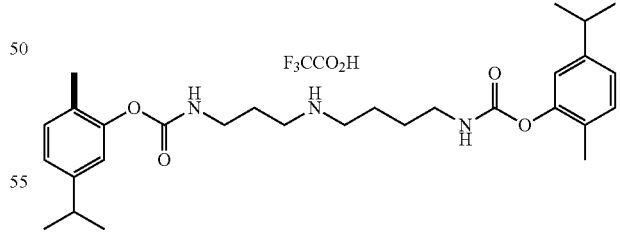

NDH4590

Slower to hydrolyze and to liberate the terpene moiety are the trifluoroacetate salts or amides as exemplified by the carvacrol-spermidine conjugate, NDH4622, with $F_3CCO_2H$

NDH4622

83% (CEES) and 100% (TPA). The similarly stabilized carvacrol-spermine bis trifluoroacetate salt conjugate, NDH4631, was assayed with 84% (CEES) and 89% (TPA) values.

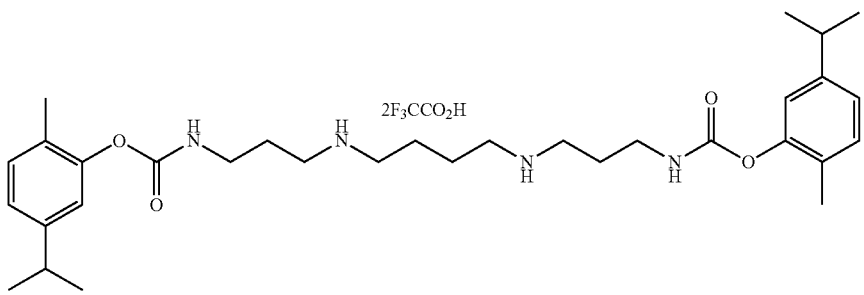

NDH4631

The covalently-attached trifluoroacetyl (as an amide) yields a very stable thymol-spermidine conjugate, NDH4616, which retained considerable anti-inflammatory activity, 76% (TPA).

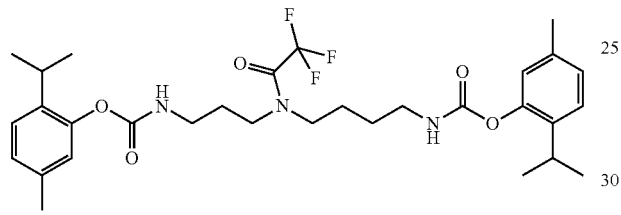

NDH4616

As an example of a Formula 5 compound, NDH4483 links two vanilloid units (vanillyl alcohol and vanillylamine) to a core valine unit. The inflammation suppression was 67% (TPA) and the FAAH $IC_{50}$ was 1.0 mM. The hydrolysis half-life without the acetyl group attached to the para-hydroxyl of the vanillyl alcohol moiety was under 5 minutes in physiological saline.

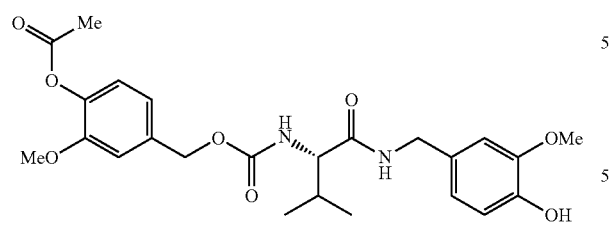

NDH4483

A modification of this Formula 5 compound in which the vanillylamine portion has been deleted (NDH4481) had the same hydrolytic instability-unless the p-hydroxyl group was acetylated—

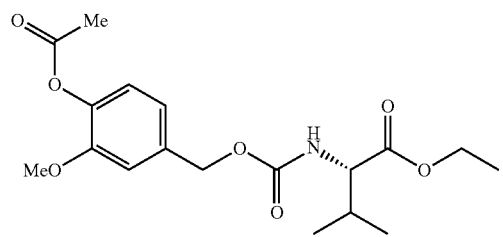

NDH4481 and possessed the same FAAH $IC_{50}$ of 1.0 mM but with a slightly improved inflammation suppression of 72% (CEES-induced) and 93% (TPA-induced).

As an example of a Formula 6 compound, NDH 4648 joins the terpene carvacrol to the amino acid valine by a carbamate bond and thence joins the terpene farnesol to that same amino acid by an ester bond.

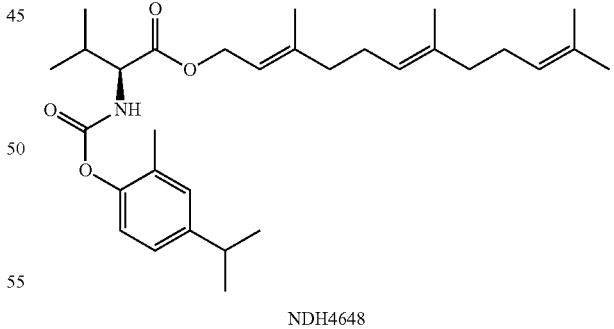

NDH4648

As an example of a Formula 7 compound, NDH 4486 links the terpene geraniol to the amino acid valine by a carbamate bond and thence joins the vanilloid vanillylamine to that same amino acid by an amide bond. The resulting conjugate showed an inflammation suppression of 91% (TPA-induced).

ASPECT I SYNTHESIS

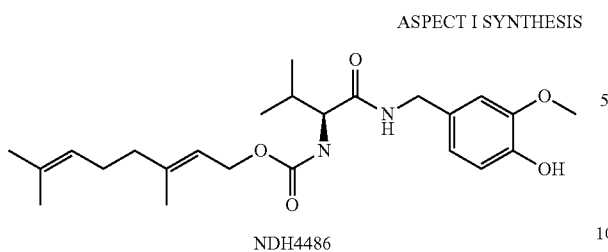

NDH4486

The compounds of the invention were synthesized by the pathways outlined in Schemes 1, 2, 3, 4, and 5, using the application of a thiazolide to transfer the —COOR unit to the polyamine, amine, or amino acid unit. The activated thiazoline is synthesized as shown in Scheme 2 if the terpene being transferred has a secondary hydroxyl group, otherwise the pathway as shown in Scheme 1 is suitable. Scheme 3 shows the transfer pathway for —COOR moiety to the polyamines; similar chemistry applies for transfer to amino acids. Scheme 3 shows how the internal secondary NH in the polyamine can have its nucleophilicity suppressed by salt formation or acetamide formation in order to prevent auto-decomposition. Scheme 4 shows how terpene and/or vanilloid moieties are transferred to an amino acid platform compound. Scheme 5 shows how terpene moieties are directly linked to vanilloid moieties (vanillylamine as example) to generate conjugates of Formula 1.

Specific examples selected from the seven Formulae of conjugates have been presented herein but these do not represent the limits of the structural possibilities. Table 1 provides examples of a wider range of synthetic targets obtainable by the experimental methods described herein and consistent with the seven Formulae of conjugates disclosed herein. Systematic names are provided for these anti-inflammatories. Table 1 includes the compounds discussed herein.

Scheme 1. Synthesis of N-alkyloxycarbonyl thiazolidine-2 thiones from 1° alcohols and N-aryloxycarbonyl thiazolidine-2 thiones from phenols: (R = terpene and/or vanilloid moiety). Suitable for alcohol moiety such as geraniol; suitable for phenol moieties such as carvacrol, thymol, eugenol, zingerone and paradol.

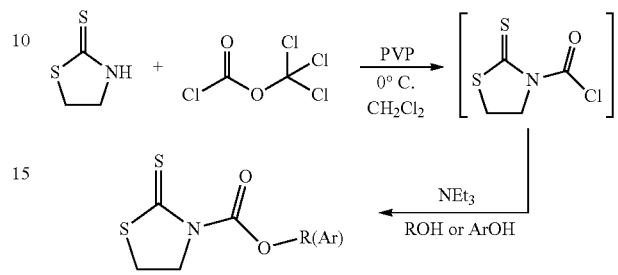

Scheme 2.
Synthesis of N-alkyloxycarbonyl thiazolidine-2 thiones from 2° alcohols:
(R = terpene and/or vanilloid moiety).
Suitable for alcohol moiety such as borneol.

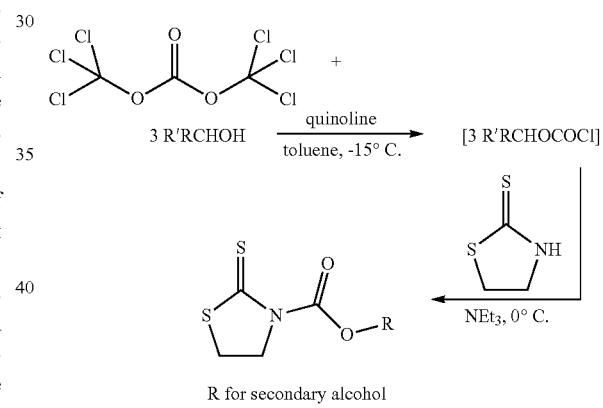

R for secondary alcohol

Scheme 3. Synthesis of salts and acetamides of polyamine conjugates: (R = terpene and/or vanilloid moiety)

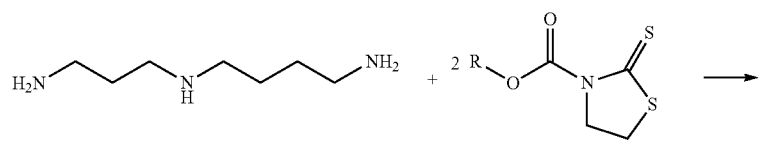

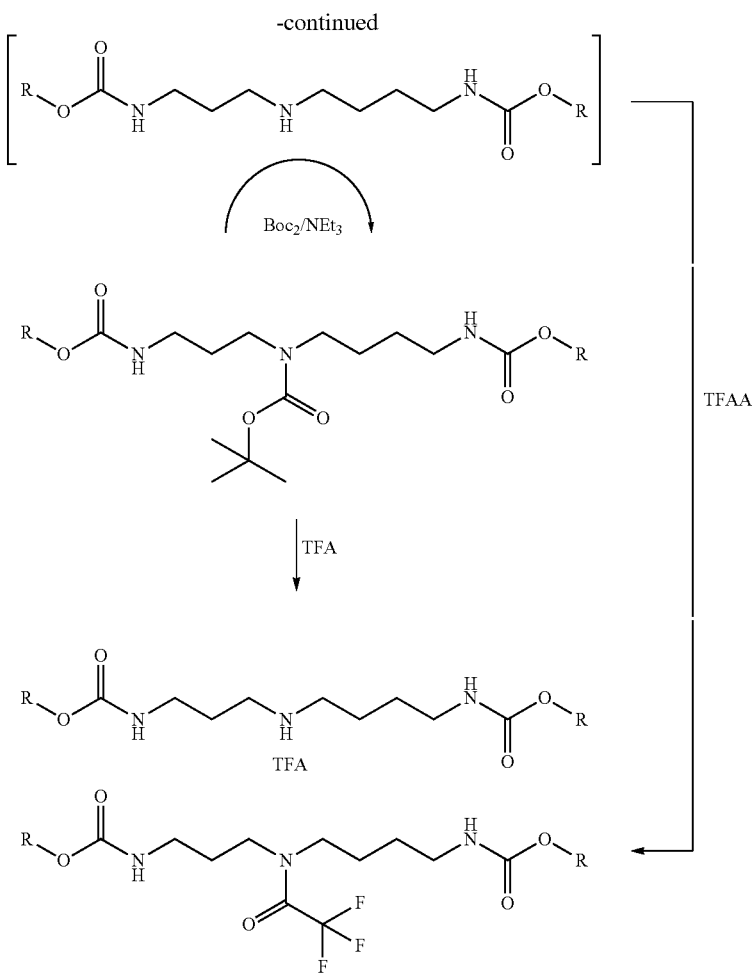
Scheme 4.
Synthesis of amino acid conjugates:
(R = terpene and/or anilloid moiety)
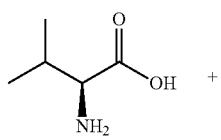
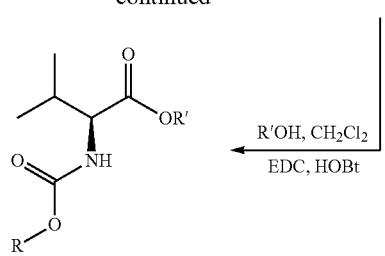
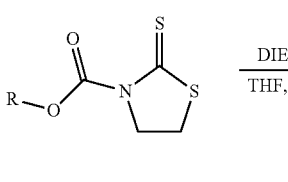
Scheme 5. Synthesis of direct vanilloid-to-terpene conjugates of Formula 1 employing vanillylamine as the model vanilloid
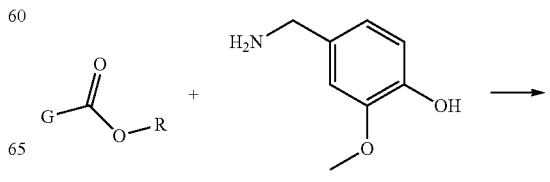

-continued

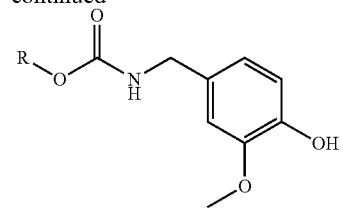

5

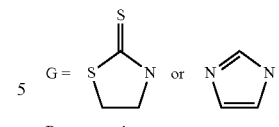

G = $\begin{array}{c}\text{S}\\ \|\\ \text{thiazolidine-2-thione}\end{array}$ or imidazole R = terpenol

TABLE 1

Structural diversity consistent with the formulae of Aspect I conjugates of the invention

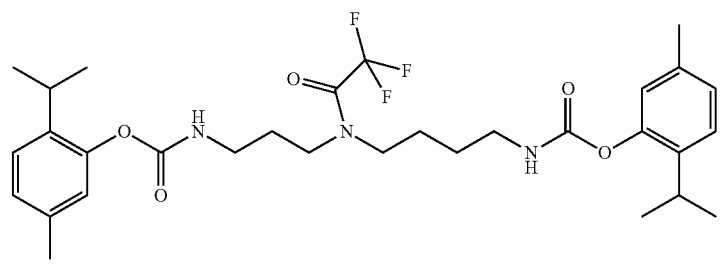 [SMILES: Cc1ccc(C(C)C)c(OC(=O)NCCCCN(CCCNC(=O)Oc2cc(C)ccc2C(C)C)C(=O)C(F)(F)F)c1]

NDH4616: 5-methyl-2-(propan-2-yl)phenyl [3-(trifluoroacetyl){4-[(5-methyl-2-(propan-2-yl)phenoxycarbonyl)amino]butyl}amino)propyl]carbamate

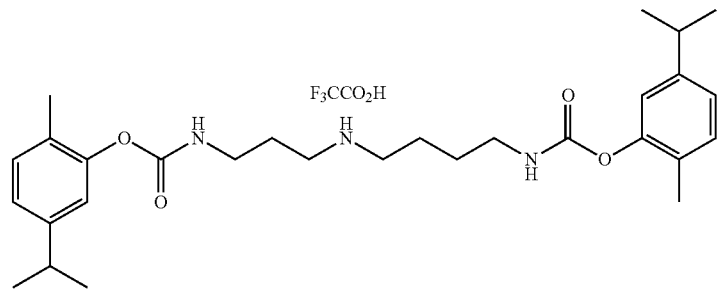 [SMILES: Cc1ccc(C(C)C)cc1OC(=O)NCCCCNCCCNC(=O)Oc1cc(C(C)C)ccc1C ; "F3CCO2H"]

NDH4622: 2-methyl-5-(propan-2-yl)phenyl [3-({4-[(2-methyl-5-(propan-2-yl)phenoxycarbonyl)amino]butyl}amino)propyl]carbamate trifluoroacetic acid salt

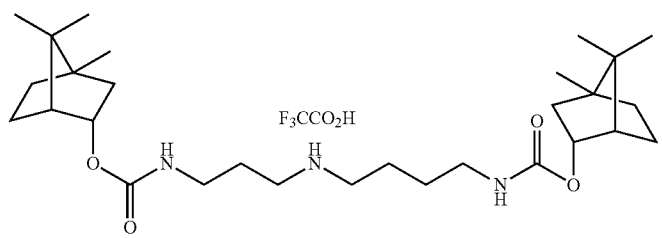 [SMILES: CC12CCC(C(OC(=O)NCCCCNCCCNC(=O)OC3CC4(C)CCC3C4(C)C)C1)C2(C)C ; "F3CCO2H"]

NDH4630: 1,7,7-trimethylbicyclo[2.2.1]hept-2-yl [3-({4-[(1,7,7-trimethylbicyclo[2.2.1]hept-2-yl oxycarbonyl)amino]butyl}amino)propyl]carbamate trifluoroacetic acid salt

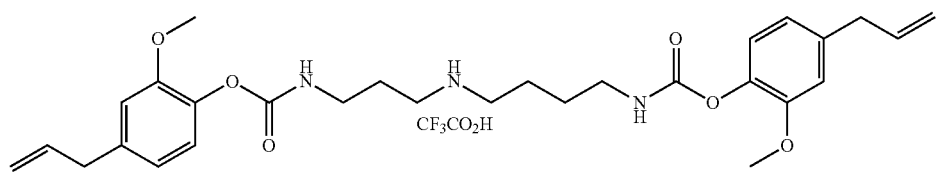 [SMILES: C=CCc1ccc(OC(=O)NCCCCNCCCNC(=O)Oc2ccc(CC=C)cc2OC)c(OC)c1 ; "CF3CO2H"]

NDH4635: 2-methoxy-4-(prop-2-en-1-yl)phenyl [3-({4-[(2-methoxy-4-(prop-2-en-1-yl)phenoxycarbonyl)amino]butyl}amino)propyl]carbamate trifluoroacetic acid salt TABLE 1-continued Structural diversity consistent with the formulae of Aspect I conjugates of the invention

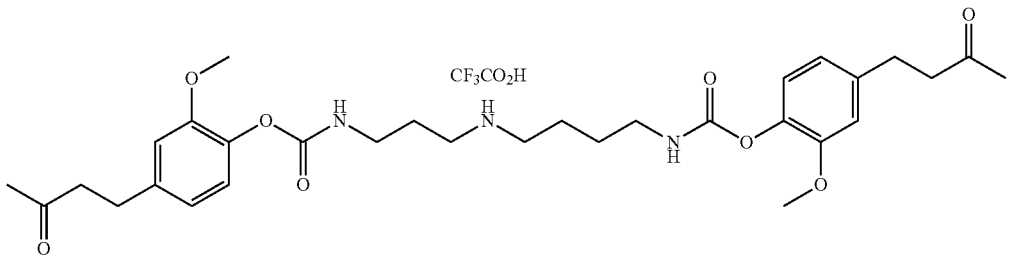 [SMILES: COc1cc(CCC(C)=O)ccc1OC(=O)NCCCCNCCCNC(=O)Oc1ccc(CCC(C)=O)cc1OC ; "CF3CO2H"]

NDH4637: 2-methoxy-4-(3-oxobutyl)phenyl [3-({4-[(2-methoxy-4-(3-oxobutyl)phenoxycarbonyl)amino]butyl}amino)propyl]carbamate trifluoroacetic acid salt

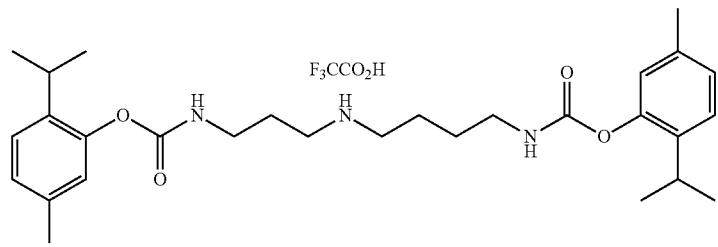 [SMILES: Cc1ccc(C(C)C)c(OC(=O)NCCCCNCCCNC(=O)Oc2cc(C)ccc2C(C)C)c1 ; "F3CCO2H"]

NDH4649: 5-methyl-2-(propan-2-yl)phenyl [3-({4-[(5-methyl-2-(propan-2-yl)phenoxycarbonyl)amino]butyl}amino)propyl]carbamate trifluoroacetic acid salt

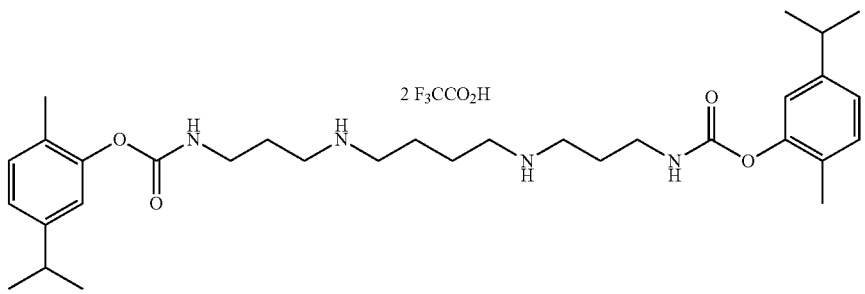

NDH4631: bis(5-isopropyl-2-methylphenyl) ((butane-1,4-diylbis(azanediyl))bis(propane-3,1-diyl))dicarbamate

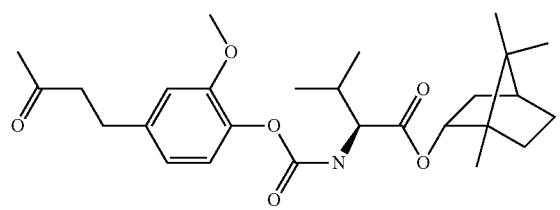 [SMILES: COc1cc(CCC(C)=O)ccc1OC(=O)N[C@H](C(=O)OC1CC2CCC1(C)C2(C)C)C(C)C]

NDH4638: (S)-(1R,2R,4S)-1,7,7-trimethylbicyclo[2.2.1]heptan-2-yl 2-(((2-methoxy-4-(3-oxobutyl)phenoxy)carbonyl)amino)-3-methylbutanoate TABLE 1-continued Structural diversity consistent with the formulae of Aspect I conjugates of the invention

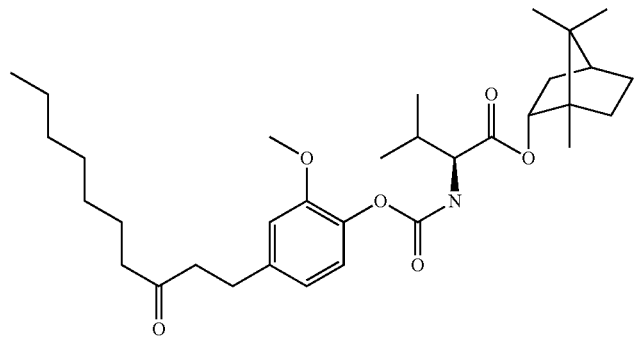 [SMILES: CCCCCCCC(=O)CCc1ccc(OC(=O)N[C@H](C(=O)OC2CC3CCC2(C)C3(C)C)C(C)C)c(OC)c1]

NDH4639: (S)-(1R,2R,4S)-1,7,7-trimethylbicyclo[2.2.1]heptan-2-yl 2-(((2-methoxy-4-(3-oxodecyl)phenoxy)carbonyl)amino)-3-methylbutanoate

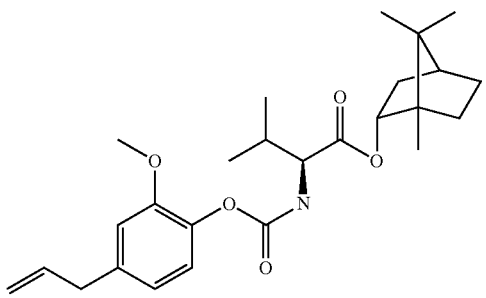 [SMILES: C=CCc1ccc(OC(=O)N[C@H](C(=O)OC2CC3CCC2(C)C3(C)C)C(C)C)c(OC)c1]

NDH4640: (S)-(1R,2R,4S)-1,7,7-trimethylbicyclo[2.2.1]heptan-2-yl 2-(((4-allyl-2-methoxyphenoxy)carbonyl)amino)-3-methylbutanoate

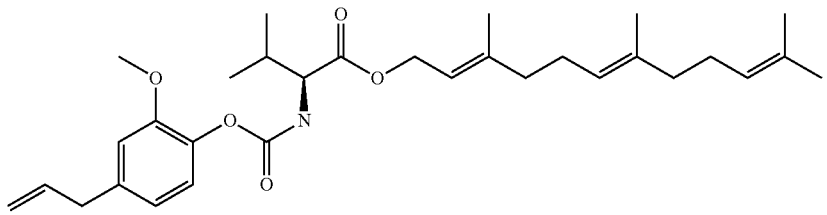 [SMILES: C=CCc1ccc(OC(=O)N[C@H](C(=O)OC/C=C(\C)CC/C=C(\C)CCC=C(C)C)C(C)C)c(OC)c1]

NDH4641: (S)-(2E,6E)-3,7,11-trimethyldodeca-2,6,10-trien-1-yl 2-(((4-allyl-2-methoxyphenoxy)carbonyl)amino)-3-methylbutanoate

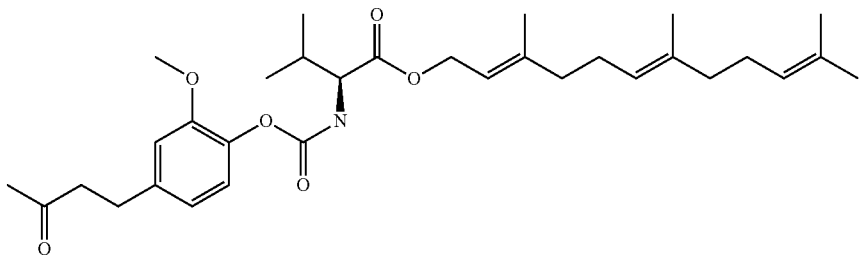 [SMILES: COc1cc(CCC(C)=O)ccc1OC(=O)N[C@H](C(=O)OC/C=C(\C)CC/C=C(\C)CCC=C(C)C)C(C)C]

NDH4642: (S)-(2E,6E)-3,7,11-trimethyldodeca-2,6,10-trien-1-yl 2-(((2-methoxy-4-(3-oxobutyl)phenoxy)carbonyl)amino)-3-methylbutanoate TABLE 1-continued Structural diversity consistent with the formulae of Aspect I conjugates of the invention

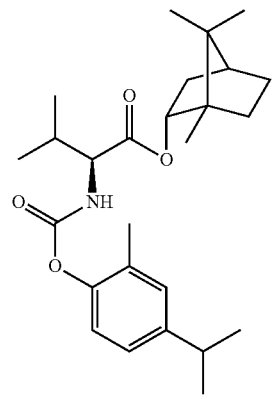 [SMILES: Cc1cc(C(C)C)ccc1OC(=O)N[C@H](C(=O)OC1CC2CCC1(C)C2(C)C)C(C)C]

NDH4647: (S)-(1R,2R,4S)-1,7,7-trimethylbicyclo[2.2.1]heptan-2-yl 2-(((4-isopropyl-2-methylphenoxy)carbonyl)amino)-3-methylbutanoate

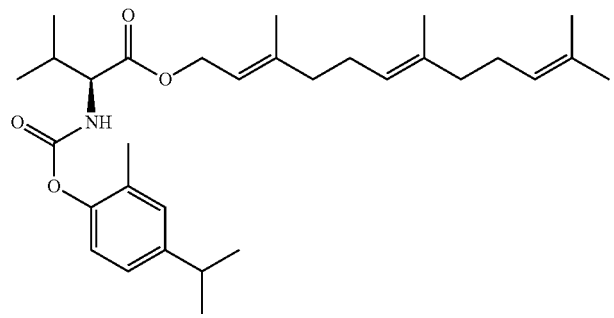 [SMILES: CC(C)=CCC/C(C)=C/CC/C(C)=C/COC(=O)[C@@H](NC(=O)Oc1ccc(C(C)C)cc1C)C(C)C]

NDH4648: (S)-(2E,6E)-3,7,11-trimethyldodeca-2,6,10-trien-1-yl 2-(((4-isopropyl-2-methylphenoxy)carbonyl)amino)-3-methylbutanoate

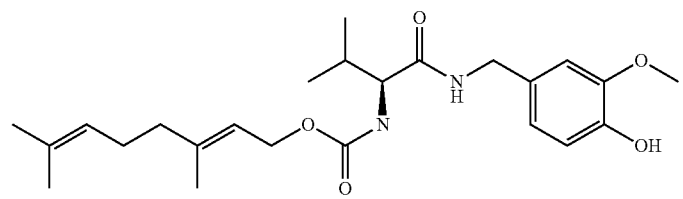 [SMILES: COc1cc(CNC(=O)[C@@H](NC(=O)OC/C=C(\C)CCC=C(C)C)C(C)C)ccc1O]

NDH4486: (S,E)-3,7-dimethylocta-2,6-dien-1-yl (1-((4-hydroxy-3-methoxybenzyl)amino)-3-methyl-1-oxobutan-2-yl)carbamate Preparation of trifluoroacetic acid salts of polyamines
A) Formation of protected carbamates

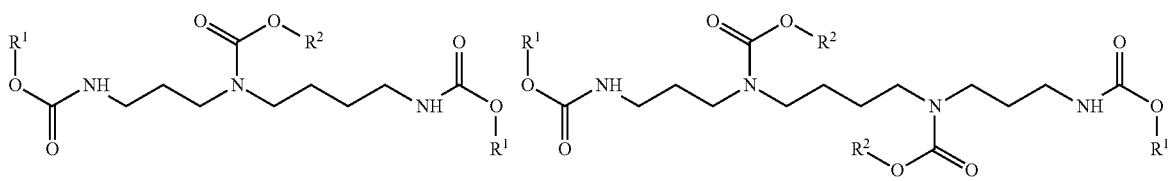

General Procedure (NDH4616, 4622, 4630, 4631, 4635, 4637 and 4649)

The polyamine (spermidine or spermine) was weighed into a round bottom flask containing a stirring bar. The amine was dissolved in dry dichloromethane ($CH_2Cl_2$) (10mL/mmol). To the stirred solution at room temperature were added two equivalents of an alkyl or aryl 2-thioxo-1,3-thiazolidine-3-carboxylate (hereafter referred to as a thiazolidine carbamate) which rendered a yellow solution. The progress of the reaction was monitored by the loss of the yellow color as well as by TLC which revealed the release of 2-mercaptothiazoline (MTA) and the disappearance of the thiazolidine carbamate. After the first step was complete triethylamine (1 equivalent) was added to the reaction flask followed by the addition of Boc anhydride (Boc$_2$) (1 equivalent). Once the second step was complete, as noted by TLC, the reaction solution was diluted with CH$_2$Cl$_2$, and the resulting solution was extracted with 1N HCl and then saturated NaCl. The organic layer was dried over MgSO$_4$ (anhydrous), filtered, concentrated on the rotary evaporator and dried under vacuum. The crude material was covered with a solution of 7:3, hexanes/ethyl acetate (EtOAc) in order to crystallize out the released MTA. The supernatant was drawn off and concentrated. The product was purified by column chromatography on silica gel eluting with 7:3, hexanes/EtOAc.

1. NDH 4622: R$_f$=0.32 (7:3, hexanes/EtOAc): Yield=76%.
2. NDH 4630: R$_f$=0.39 (7:3, hexanes/EtOAc); Yield=57%.
3. NDH 4649: R$_f$=0.27 (7:3, hexanes/EtOAc); Yield=63%.
4. NDH 4631: Removal of MTA from the crude material was accomplished using 3:2, hexanes/EtOAc. Column purification was carried out using 96:4, CH$_2$Cl$_2$/acetone as eluant. R$_f$=0.25 (96:4, CH$_2$Cl$_2$/acetone): Yield=83%.
5. NDH 4635: The crude material was purified by column chromatography, without removing MTA, first using 98:2, CH$_2$Cl$_2$/MeOH and for the second column 96:4, CH$_2$Cl$_2$/acetone. R$_f$=0.21 (96:4, CH$_2$Cl$_2$/acetone): Yield=77%.
6. NDH 4637: The crude material was purified by column chromatography, without removing MTA, using a gradient of 94:6, CH$_2$Cl$_2$/acetone to 9:1, CH$_2$Cl$_2$/acetone and then 97:3, CH$_2$Cl$_2$/MeOH. R$_f$=0.06 (95:5, CH$_2$Cl$_2$/acetone); Yield=100%.
7. NDH 4616: Upon completion of the first step, 1.5 equivalents of ethyl trifluoroacetate were added in place of the Boc$_2$ and triethylamine, and the reaction mixture was stirred overnight. The product crystallized out of the reaction, and was collected by suction filtration and rinsed with CH$_2$Cl$_2$. Exact mass (ESI) calculated for C$_{29}$H$_{44}$N$_3$O$_4$ [M+H]498.3326 found 498.3334. The exact mass represents the compound resulting from loss of the trifluoroacetyl group. R$_f$=0.70 (9:1. CH$_2$Cl$_2$/MeOH): mp=190-191° C.; Yield=51%.

B) Formation of Trifluoroacetic Acid (TFA) Salts

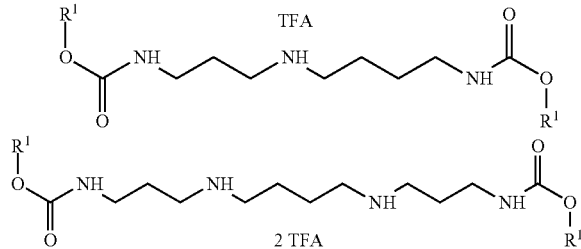

General procedure (NDH4616, 4622, 4630, 4631, 4635, 4637 and 4649)

The Boc-containing protected carbamate was dissolved in anhydrous CH$_2$Cl$_2$ (20 mL/mmol). Trifluoroacetic acid (4 mL/mmol) was added at room temperature. The reaction solution was stirred, and the progress of the reaction was monitored by TLC (7:3, hexanes/EtOAc). The deprotection was complete in 1-2 h. The volatiles were removed by distillation employing an aspirator vacuum. The residue was frozen on liquid N$_2$ and dried under high vacuum. The dry product was covered with diisopropyl ether and the solid that separated was triturated and collected by suction filtration.

1. NDH 4622: Exact mass (ESI) calculated for C$_{29}$H$_{44}$N$_3$O$_4$ [M+H]498.3326, found 498.3334. White powder; Yield=68%.
2. NDH 4631: Exact mass (ESI) calculated for C$_{32}$H$_{51}$N$_4$O$_4$ [M+H]555.3905, found 555.3896. White solid; Yield=72%.
3. NDH 4649: Exact mass (ESI) calculated for C$_{29}$H$_{44}$N$_3$O$_4$ [M+H]498.3326, found 498.3324. White solid; Yield=95%
4. NDH 4630: Exact mass (ESI) calculated for C$_{29}$H$_{52}$N$_3$O$_4$ [M+H]506.3952, found 506.3973. Viscous oil; Yield=100%.
5. NDH 4635: The reaction was monitored by using 98:2, CH$_2$Cl$_2$/MeOH as the TLC solvent. The crude residue was covered with diethyl ether and triturated in order to isolate the pure product. Exact mass (ESI) calculated for C$_{29}$H$_{40}$N$_3$O$_6$ [M+H]526.2912, found 526.2944. White powder; Yield=88%.
6. NDH 4637: The reaction was monitored using 96:4, CH$_2$Cl$_2$/acetone as the TLC solvent. The crude residue was covered with diethyl ether and triturated in order to isolate the pure product. Exact mass (ESI) calculated for C$_{31}$H$_{44}$N$_3$O$_8$ [M+H]586.3123, found 586.3141. White solid; Yield=85%.

NMR Data

1) NDH 4622

$^1$HNMR (methanol-d$_4$) δ: 7.14-7.10 (m, 2H, 2×ArH-3), 7.02-6.98 (m, 2H, 2×ArH-4), 6.88-6.83 (m, 2H, 2×ArH-6), 3.22 (bt, 2H, HNCH$_2$CH$_2$CH$_2$N), 3.11-3.02 (m, 4H, CH$_2$NHCH$_2$), 2.89-2.81 (m, 2H, 2×HC(CH$_3$)$_2$), 2.15-2.11 (overlapping singlets, 6H, 2×Ar-CH$_3$), 1.97-1.89 (m, 2H, NHCH$_2$CH$_2$CH$_2$NH), 1.79-1.69 (m, 2H, NHCH$_2$CH$_2$—CH$_2$NHCO), 1.69-1.60 (m, 2H, NHCH$_2$CH$_2$CH$_2$NHCO), and 1.22-1.18 (overlapping doublets, 12H, $^3$J=6.9 Hz, 2×ArCH(CH$_3$)$_2$). Note: The protons OCHNCH$_2$CH$_2$NH are masked beneath the methanol-d$_4$ CH$_3$ peak centered at δ3.30.

2) NDH 4630

$^1$HNMR (CDCl$_3$+D$_2$O) δ: 3.31 (bt, 2H, OCHNCH$_2$CH$_2$CH$_2$NH), 3.17 (t, 2H, $^3$J=6.70 Hz, NHCH$_2$CH$_2$CH$_2$CH$_2$NHCO), 3.05-2.92 (m, 4H, CH$_2$NHCH$_2$), 2.36-2.24 (m, 2×1H, 3-H exo), 1.98-1.90 (m, 2H, NHCH$_2$CH$_2$CH$_2$NH), 1.90-1.55 (m, 10 H, NHCH$_2$CH$_2$CH$_2$CH$_2$NHCO, 2×bornyl H-4, 2×bornyl H-5 exo and 2×bornyl H-6 endo), 1.30-1.16 (m, 4H, 2×bornyl H-5 endo and 2×bornyl H-6 exo), 1.00-0.94 (m, 2H, 2×bornyl H-3 endo), 0.88-0.86 (bd, 6H, 2×bornyl C-7 CH$_3$), 0.85-0.83 (bd, 6H, 2×bornyl C-7 CH$_3$) and 0.81 (bs, 6H, 2×bornyl C-1 CH$_3$). Note: The bornyl C-2 protons are masked beneath the D$_2$O peak.

3) NDH 4631

$^1$HNMR (methanol-d$_4$) δ: 7.16-7.10 (bd, 2H, 2×ArH-3), 7.04-6.98 (n 2H, 2×ArH-4), 6.89-6.84 (bd, 2H, 2×Ar-6), 3.11-2.99, (m, 8H, CH$_2$NCH$_2$CH$_2$CH$_2$CH$_2$NCH$_2$), 2.90-2.81 (m, 2H, 2×CH(CH$_3$)$_2$), 2.14 (bs, 6H, 2×ArCH$_3$), 1.97-1.89 (m, 4H, 2×NCH$_2$CH$_2$CH$_2$N), 1.80-1.72 (m, 4H, NCH$_2$CH$_2$CH$_2$CH$_2$N), and 1.21 (bd, 12H, $^3$J=6.95 Hz, 2×HC(CH$_3$)$_2$). Note: The protons 2×OCNHCH$_2$ are masked beneath the methanol-d$_4$ CH$_3$ peak centered at δ3.30.

4) NDH 4635

$^1$HNMR (methanol-d$_4$) δ: 6.98-6.90 (2 sets of doublets, 2H, $^3$J=8.0 and 8.05 Hz, 2×ArH-6), 6.90-6.84 (2 sets of doublets, 2H, $^4$J=1.65 Hz, 2×ArH-3), 6.79-6.71 (n, 2H, 2×ArH-5), 60.1-5.90 (m, 2H, 2×CH$_2$=CH), 5.12-5.01 (m, 4H, 2×CH$_2$—CH), 3.80 (s, 3H, Ar—OCH$_3$), 3.78 (s, 3H, Ar—OCH$_3$), 3.36 (overlapping doublets, 4H, $^3$J=6.65 Hz, 2×ArCH$_2$—CH=CH$_2$), 3.22-3.16 (m, 2H, NHCH$_2$CH$_2$CH$_2$CH$_2$NHCO), 3.12-3.00 (m, 4H, CH$_2$NHC H$_2$), 1.97-1.87 (m, 2H, NCH$_2$CH$_2$CH$_2$N), 1.80-1.68 (m, 2H, NHCH$_2$CH$_2$CH$_2$CH$_2$NHCO), and 1.67-1.57 (m, 2H, NHCH$_2$CH$_2$CH$_2$CH$_2$NHCO). Note: The protons OCHNCH$_2$CH$_2$CH$_2$NH are masked beneath the methanol-d$_4$ CH$_3$ peak centered at δ3.30.

5) NDH 4637

$^1$HNMR (methanol-d$_4$) δ: 6.96-6.87 (m, 4H, 2×ArH-3 and 2×ArH-6), 6.80-6.73 (m, 2H, 2×ArH-5), 3.84-3.74 (m, 6H, 2×Ar—OCH$_3$). 3.21-3.14 (m, 2H, OCHNCH$_2$CH$_2$CH$_2$NH), 3.12-3.00 (m, 4H, CH$_2$NHCH$_2$), 2.88-2.76 (m, 8H, 2×ArCH$_2$CH$_2$CO), 2.12-2.11 (overlapping singlets, 6H, 2×COCH$_3$), 1.96-1.85 (m, 2H, NCH$_2$CH$_2$CH$_2$N), 1.79-1.68 (m, 2H, NHCH$_2$CH$_2$CH$_2$CH$_2$NHCO) and 1.67-1.58 (m, 2H, NHCH$_2$CH$_2$CH$_2$CH$_2$NHCO). Note: The protons OCHNCH$_2$CH$_2$CH$_2$NH are masked beneath the methanol-d$_4$ CH$_3$ peak centered at δ3.30.

6) NDH 4649

$^1$HNMR (methanol-d$_4$) δ: 7.24-7.13 (m, 2H, ArH-3), 7.06-6.95 (m, 2H, ArH-4), 6.86-6.75 (m, 2H, ArH-6), 3.25-3.21 (m, 2H, NHCH$_2$CH$_2$CH$_2$CH$_2$NHCO), 3.13-2.98 (m, 6H, 2×CH(CH$_3$)$_2$ and CH$_2$NHCH$_2$), 2.30 (bs, 6H, 2×ArCH$_3$), 1.99-1.88 (m, 2H, NCH$_2$CH$_2$CH$_2$N). 1.82-1.70 (m, 2H, NHCH$_2$CH$_2$CH$_2$CH$_2$NCO) and 1.70-1.60 (m, 2H, NHCH$_2$CH$_2$CH$_2$CH$_2$NCO). Note: The protons OCNCH$_2$CH$_2$CH$_2$NH are masked beneath the methanol-d$_4$ CH$_3$ peak centered at δ3.30.

7) NDH 4616

$^1$HNMR (acetone-d$_6$) δ: 7.22 (bs, 2H (partially exchanged), 2×NH), 7.17 (apparent triplet, 2H, $^3$J=7.4 Hz, 2×ArH-3), 6.98 (apparent triplet, 2H, $^3$J=7.8 Hz, 2×ArH-4), 6.87 (s, 1H, ArH-6), 6.84 (s, 1H, ArH-6), 3.41-3.35 (m, 2H, HNCH$_2$CH$_2$CH$_2$N), 3.28-3.16 (m, 6H, NHCH$_2$CH$_2$CH$_2$NCH$_2$CH$_2$CH$_2$NH), 3.10-3.04 (m, 2H, Ar-CH(CH$_3$)$_2$), 2.08 (m, 2H, HNCH$_2$CH$_2$CH$_2$N), 1.93-1.84 (m, 2H, —NCH$_2$CH$_2$CH$_2$CH$_2$NH—), 1.72-1.65 (m, 2H, —NCH$_2$CH$_2$CH$_2$NH—) and 1.20-1.12 (overlapping doublets, 12H, $^3$J=6.85 Hz. 2×ArCH(CH$_3$)$_2$).

Preparation of Valine-Based Compounds
A) Carbamate Formation

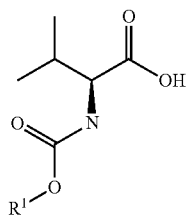

A flask containing a stirring bar was charged with the N-acyl thiazolidine-2-thione (1 eq) and L-valine (1.05 eq). To the flask was added THF (5 mL/mmol of the N-acyl thiazolidine-2-thione), and the mixture was stirred until all the N-acyl thiazolidine-2-thione dissolved. Water (5 mL/mmol) was then added followed by N,N-diisopropylethylamine (2 eq), and the resulting two-phase system was stirred vigorously at room temperature. The progress of the reaction was monitored by TLC (9:1, CH$_2$Cl$_2$/MeOH, v/v) and by the disappearance of the yellow color originating from the N-acyl thiazolidine-2-thione. When the reaction was complete, the solution was diluted with CH$_2$Cl$_2$ and extracted with 1N HCl. The organic layer was concentrated on the rotary evaporator, the residue taken up in Et$_2$O, and the resulting ether layer was extracted with saturated NaHCO$_3$. The aqueous layer was then washed with Et$_2$O. The aqueous phase was acidified to pH=2-3 with 4N HCl. The resulting mixture was extracted with CH$_2$Cl$_2$. The organic layer was dried over MgSO$_4$ (anhydrous), filtered, concentrated on the rotary evaporator and dried under high vacuum. The product was used in the next step without further purification.

B) Condensation Reactions
1. Amide Formation

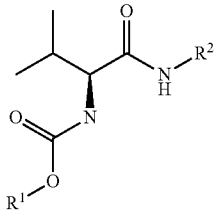

The N-acylated amino acid (1 eq), 1-Hydroxybenzotriazole (HOBt) (1.05 eq) and HMBA hydrochloride (1.05 eq) were placed in a round bottom flask equipped with a stirring bar and fitted with a rubber septum. Dry CH$_2$Cl$_2$ (4 mL/mmol) and NEt$_3$ (1.05 eq) were added under positive N$_2$ pressure via a syringe through the rubber septum. The flask was immersed in an ice bath, and the reaction mixture was stirred. After sufficient chilling, 1-Ethyl-3-(3-dimethylaminopropyl)carbodiimide (EDC) (1.05 eq) was added in one portion, and the reaction mixture was allowed to stir to room temperature overnight. TLC (96:4, CH$_2$Cl$_2$/MeOH, v/v) revealed completion of reaction. The reaction mixture was diluted with CH$_2$Cl$_2$ and washed with 1N HCl, H$_2$O and saturated NaCl. The organic phase was dried over MgSO$_4$ (anhydrous), filtered and concentrated on the rotary evaporator. The residue was dried under high vacuum, and the crude product was purified by column chromatography on silica gel eluting with 9:1, CH$_2$Cl$_2$/acetone, v/v.

NDH 4486: Mp=135-136° C.; R$_f$=0.54 (9:1, CH$_2$Cl$_2$/acetone); Yield=68%. Exact mass (ESI) calculated for C$_{24}$H$_{37}$N$_2$O$_5$ [M+H]433.2697. found 433.2676.

2. Ester Formation

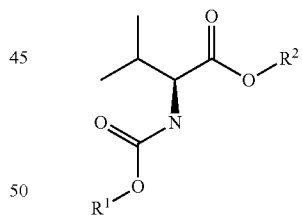

The preparation of esters was carried out as described for amides with the exception of replacing HOBt with 0.2 eq of DMAP. TLC analysis was performed using 7:3, hexanes/EtOAC, v/V while chromatographic purification was carried out using 8:2, hexanes/EtOAC, v/v.

1. NDH 4638: The crude material was purified by column chromatography eluting with 7:3, hexanes/EtOAc. R$_f$=0.27 (7:3, hexanes/EtOAc); Yield=47%. Exact mass (ESI) calculated for C$_{27}$H$_{40}$NO$_6$ [M+H]474.2850. found 474.2878.

2. NDH 4642: The crude material was purified by column chromatography eluting with 7:3, hexanes/EtOAc. R$_f$=0.32 (7:3, hexanes/EtOAc); Yield=61%. Exact mass (ESI) calculated for C$_{32}$H$_{48}$NO$_6$ [M+H]542.3476. found 542.3494.

3. NDH 4639: The reaction solution was concentrated, and the residue taken up in EtOAc. The organic layer was extracted with a small amount of water, saturated NaHCO$_3$, water, and finally saturated NaCl. The crude product was purified twice by column chromatography-first eluting with 8:2, hexanes/EtOAc and then 94:6, CH$_2$Cl$_2$/Et$_2$O. R$_f$=0.36 (8:2, hexanes/EtOAc); Yield=24%. Exact mass (ESI) calculated for C$_{33}$H$_{52}$NO$_6$ [M+H]558.3789. found 558.3809.

4. NDH 4647: The reaction solution was concentrated, and the residue taken up in EtOAc. The organic layer was extracted with a small amount of water, saturated NaHCO$_3$, water, and finally saturated NaCl. The crude material was purified by column chromatography eluting with 8:2, hexanes/EtOAc. R$_f$=0.70 (8:2. hexanes/EtOAc); Yield=43%. Exact mass (ESI) calculated for C$_{26}$H$_{40}$NO$_4$ [M+H]430.2952. found 430.2968.

5. NDH 4648: The reaction solution was concentrated, and the residue taken up in EtOAc. The organic layer was extracted with a small amount of water, saturated NaHCO$_3$, water, and finally saturated NaCl. The crude material was purified by column chromatography eluting with 8:2, hexanes/EtOAc. R$_f$=0.69 (8:2, hexanes/EtOAc); Yield=62%. Exact mass (ESI) calculated for C$_{31}$H$_{47}$NO$_4$Na [M+Na]520.3397. found 520.3429.

6. NDH 4640: The reaction solution was concentrated, and the residue taken up in EtOAc. The organic layer was extracted with a small amount of water, saturated NaHCO$_3$, water, and finally saturated NaCl. The crude material was purified by column chromatography eluting with 8:1:1 (CH$_2$Cl$_2$/DIPE/hexanes). R$_f$=0.89 (8:1:1, CH$_2$Cl$_2$/DIPE/hexanes); Yield=57%. Exact mass (ESI) calculated for C$_{26}$H$_{38}$NO$_5$ [M+H]444.2744. found 444.2750.

7. NDH 4641: The reaction solution was concentrated, and the residue taken up in EtOAc. The organic layer was extracted with a small amount of water, saturated NaHCO$_3$, water, and finally saturated NaCl. The crude material was purified by column chromatography eluting with 8:1:1(CH$_2$Cl$_2$/DIPE/hexanes). R$_f$=0.92 (8:1:1, CH$_2$Cl$_2$/DIPE/hexanes): Yield=64%. Exact mass (ESI) calculated for C$_{31}$H$_{46}$NO$_5$ [M+H]512.3370. found 512.3391.

NMR Data

1) NDH 4486

$^1$HNMR (CDCl$_3$) δ6.83 (d, 1H, $^3$J=8.0 Hz, ArH). 6.76 (d, 1H, $^4$J=1.85 Hz, ArH). 6.72 (dd, 1H, $^3$J=8.1 Hz, $^4$J=1.85 Hz, ArH), 6.12 (bs, 1H, amide NH), 5.57 (s, 1H, ArOH), 5.30 (bs, 1H, O—CH$_2$CH=), 5.16 (d, 1H, $^3$J=7.4 Hz, carbamate NH), 5.06 (m, 1H, (CH$_3$)$_2$—C=CH—), 4.60-4.50 (m, 2H, C(O)O—CH$_2$—), 4.41-4.29 (2×dd, 2H, $^2$J=14.5 Hz, $^3$J=5.5 Hz, Ar—CH$_2$—N), 3.93 (dd, 1H, $^3$J$_{NH}$=8.7 Hz, $^3$J$_{CH}$=6.1 Hz, CO—CH), 3.85 (s, 3H, Ar—O—CH$_3$). 2.22-2.10 (m, 1H, CH—(CH$_3$)$_2$), 2.10-2.08 (m, 4H, =C—CH$_2$—CH$_2$—C=), 1.69-1.63 (m, 6H, =(CH$_3$)$_2$), 1.58 (s, 3H, CH$_3$—C=), 0.95 (d, 3H, $^3$J=6.8 Hz, CH(CH$_3$)—CH$_3$) and 0.90 (d, 3H, $^3$J=6.8 Hz, CH(CH$_3$)—CH$_3$). Exact mass (ESI) Calculated for C$_{24}$H$_{37}$N$_2$O$_5$ [M+1]433.2697. found 433.2676.

2) NDH 4631

$^1$HNMR (methanol-d$_4$) δ7.16-7.10 (bd, 2H, 2×ArH-3), 7.04-6.98 (m, 2H, 2×ArH-4), 6.89-6.84 (bd, 2H, 2×Ar-6), 3.11-2.99, (m, 8H, CH$_2$NCH$_2$CH$_2$CH$_2$CH$_2$NCH$_2$), 2.90-2.81 (m, 2H, 2×CH(CH$_3$)$_2$), 2.14 (bs, 6H, 2×ArCH$_3$), 1.97-1.89 (m, 4H, 2×NCH$_2$CH$_2$CH$_2$N), 1.80-1.72 (m, 4H, NCH$_2$CH$_2$CH$_2$CH$_2$N), and 1.21 (bd, 12H, $^3$J=6.95 Hz, 2×HC(CH$_3$)$_2$). Note: The protons 2×OCNHCH$_2$ are masked beneath the methanol-d$_4$ CH$_3$ peak centered at δ3.30.

3) NDH 4638

$^1$HNMR (CDCl$_3$) δ6.97 (d, 1H, J=8.05 Hz, ArH-6), 6.75 (d, 1H, $^4$J=1.8 Hz, ArH-3), 6.71 (dd, 1H, $^3$J=8.05 Hz, $^4$J=1.8 Hz, ArH-5), 5.60 (d1H, $^3$J=9.05 Hz, NH), 4.90 (bd, 1H, $^3$J=9.55 Hz, bornyl H-2), 4.34 (dd, 1H, J=8.9 Hz, $^4$J=4.5 Hz, CO—CH), 3.77 (s, 3H, ArOCH$_3$), 2.85 (t, 2H, $^3$J=7.5 Hz, ArCH$_2$CH$_2$CO), 2.73 (t 2H, $^3$J=7.45 Hz, ArCH$_2$CH$_2$CO), 2.41-2.36 (m, 1H, bornyl H-3exo), 2.27-2.20 (n, 1H, (CH$_3$)$_2$CH), 2.13 (s, 3H, COCH$_3$), 1.94-1.89 (m, 1H, bornyl H-6 endo), 1.78-1.72 (m, 1H, bornyl H-5 exo), 1.68 (t, 1H, J=4.40 Hz, bornyl H-4), 1.37-1.28 (m, 1H, bornyl H-6 co), 1.25-1.16 (m, 1H, bornyl H-5 endo), 1.02 (d, 3H, $^3$J=6.85 Hz, CH$_3$(CH$_3$)CH—), 0.99-0.94 (m, 4H, bornyl H-3 endo and CH$_3$(CH$_3$)CH—), 0.89 (s, 3H, one bornyl C-7 CH$_3$), 0.87 (s, 3H, one bornyl C-7 CH$_3$) and 0.84 (s, 3H, bornyl C-1 CH$_3$).

4) NDH 4639

$^1$HNMR (CDCl$_3$) δ6.97 (d, 1H, $^3$J=8.05 Hz, ArH-6), 6.75 (d, 1H, $^4$J=1.8 Hz, ArH-3), 6.71 (dd, 1H, $^3$J=8.10 Hz, $^4$J=1.8 Hz, ArH-5), 5.60 (d, 1H, $^3$J=8.95 Hz, NH), 4.91 (bd, 1H, $^3$J=9.60 Hz, bornyl H-2), 4.34 (dd, 1H, $^3$J=8.95 Hz, $^4$J=4.55 Hz, CHCO), 2.84 (t, 2H, $^3$J=7.58 Hz, ArCH$_2$—), 2.69 (t, 2H, $^3$J=7.58 Hz, ArCH$_2$CH$_2$CO—), 2.41-2.34 (m, 3H, bornyl H-3 exo and ArCH$_2$CH$_2$COCH$_2$—), 2.27-2.20 (m, 1H, (CH$_3$)$_2$CH—), 1.94-1.89 (m, 1H, bornyl H-6 endo), 1.78-1.72 (m, 1H, bornyl H-5 exo), 1.68 (t, 1H, $^3$J=4.42 Hz, bornyl H-4), 1.58-1.50 (m, —COCH$_2$CH$_2$(CH$_2$)$_4$CH$_3$ masked beneath D$_2$O peak), 1.36-1.17 (m, 10H, —COCH$_2$CH$_2$(CH$_2$)$_4$CH$_3$, bornyl H-5 endo and bornyl H-6 exo), 1.02 (d, 3H, $^3$J=6.85 Hz, CH$_3$(CH$_3$)CH—). 1.00-0.93 (m, 4H, CH$_3$(CH$_3$)CH— and bornyl H-3 endo) 0.89 (s, 3H, one bornyl C-7 CH$_3$) and 0.86-0.83 (n m, 9H, one bornyl C-7 CH$_3$, bornyl C-1 CH$_3$ and —CO(CH$_2$)$_6$CH$_3$).

5) NDH 4640

$^1$HNMR (CDCl$_3$) δ7.01 (d, 1H, $^3$J=7.75 Hz, ArH-6), 6.75 (d, 1H, $^4$J=1.6 Hz, ArH-3), 6.73 (d, 1H, $^3$J=8.05 Hz, ArH-5), 5.97-5.89 (m, 1H, ArCH$_2$CH=CH$_2$), 5.61 (d, 1H, $^3$J=8.95 Hz, NH), 5.10-5.04 (m, 2H, ArCH$_2$CH=CH$_2$), 4.92-4.89 (m, 1H, bornyl H-2), 4.35 (dd, 1H, J$_{NH}$=8.95 Hz, J$_{CH}$=4.55 Hz, —CH(NH)CO—), 3.80 (s, 3H, ArOCH$_3$), 3.34 (d, 2H, J=6.70 Hz, ArCH$_2$CH=CH$_2$), 2.42-2.34 (m, 1H, bornyl H-3 exo), 1.95-1.89 (m, 1H, bornyl H-6 endo), 1.78-1.71 (m, 1H, bornyl H-5 exo), 1.68 (t, 1H, J=4.45 Hz, bornyl H-4), 1.37-1.28 (m, 1H, bornyl H-6 exo), 1.25-1.16 (m, 1H, bornyl H-5 endo), 1.03 (d, 3H, $^3$J=6.90 Hz, CH$_3$(CH$_3$)CH—), 0.99-0.94 (m, 4H, bornyl H-3 endo and CH$_3$(CH$_3$)CH—), 0.89 (s 3H, one bornyl C-7 CH$_3$), 0.86 (s, 3H, one bornyl C-7 CH$_3$) and 0.84 (s, 3H, bonyl C-1 CH$_3$).

6) NDH 4641

$^1$HNMR (CDCl$_3$) δ7.01 (d, 1H, $^3$J=8.0 Hz, ArH-6), 6.74 (d, 1H, $^4$J=1.65 Hz. ArH-3), 6.72 (dd, 1H, $^3$J=8.0 Hz, $^4$J=1.8 Hz. ArH-5), 5.96-5.88 (m, 1H, ArCH$_2$CH=CH$_2$), 5.60 (d, 1H, $^3$J=9.1 Hz. NH), 5.35 (bt, 1H, J=7.15 Hz, —OCH$_2$CH=C—), 5.13-5.03 (m, 4H, ArCH$_2$CH=CH$_2$ and 2 vinyl H of farnesyl chain), 4.72-4.61 (m, 2H, —OCH$_2$CH=C—), 4.33 (dd, 1H, J$_{NH}$=9.15 Hz, J$_{CH}$=4.6 Hz, (CH$_3$)$_2$CHCHCO), 2.25-2.17 (m, 1H, (CH$_3$)$_2$CH—), 2.13-1.93 (m, 8H, 4 allylic —CH$_2$— of farnesyl chain), 1.70 (s, 3H, —OCH$_2$C=C(CH$_3$)—), 1.66 (s, 3H, center CH$_3$ of farnesyl chain), 1.58 (s, 6H, —C=C(CH$_3$)$_2$), 0.996 (d, 3H, $^3$J=6.85 Hz, CH$_3$(CH$_3$)CH—) and 0.917 (d, 3H, $^3$J=6.90 Hz, CH$_3$(CH$_3$)CH—).

7) NDH 4642

$^1$HNMR (CDCl$_3$) δ6.97 (d, 1H, $^3$J=8.0 Hz, ArH-6), 6.75 (d, 1H, $^4$J=1.85 Hz, ArH-3), 6.70 (dd, 1H, $^3$J=8.05 Hz, $^4J$=1.85 Hz, ArH-5), 5.60 (d, 1H, $^3J$=9.1 Hz, NH). 5.34 (m, 1H, —OCH$_2$CH̲=C—), 5.12-5.04 (m, 2H, 2 vinyl H of farnesyl chain), 4.72-4.60 (m, 2H, —OCH̲$_2$CH=C—), 4.33 (dd, 1H, J$_{NH}$=9.15 Hz, J$_{CH}$=4.6 Hz, (CH$_3$)$_2$CHCH̲CO), 3.79 (s, 3H, ArOCH$_3$), 2.84 (t, 2H, $^3J$=7.5 Hz, ArCH$_2$—), 2.73 (t, 2H, $^3J$=7.5 Hz, ArCH$_2$CH̲$_2$CO—), 2.26-2.17 (m, 1H, (CH$_3$)$_2$CH̲—), 2.12 (s, 3H, —COCH$_3$), 2.11-1.93 (m, 8H, 4 allylic —CH$_2$— of farnesyl chain), 1.70 (2, 3H, —OCH$_2$CH=C(CH̲$_3$)—), 1.66 (s, 3H, center CH̲$_3$ of farnesyl chain), 1.58 (s, 6H, —C=C(CH̲$_3$)$_2$), 0.99 (d, 3H, $^3J$=6.8 Hz, CH̲$_3$(CH$_3$)CH—) and 0.91 (d, 3H, $^3J$=6.90 Hz, CH$_3$(CH̲$_3$)CH—).

8) NDH 4647

$^1$HNMR (CDCl$_3$) δ7.10 (d, 1H, $^3J$=7.75 Hz, ArH-6), 6.97 (dd, 1H, $^3J$=7.70 Hz, $^4J$=1.55 Hz, ArH-5), 6.91 (s, 1H, ArH-3), 5.54 (d, 1H, $^3J$=8.95 Hz, NH), 4.97-4.87 (m, 1H, bornyl H-2), 4.37 (dd, 1H, $^3J$=9.05 Hz and 4.45 Hz, COCH), 2.84 (septet, 1H, $^3J$=6.96 Hz, CH̲(CH$_3$)$_2$), 2.44-2.35 (m, 1H, bornyl H-3 exo), 2.30-2.21 (m, 1H, (CH$_3$)$_2$CH̲CH(NH)CO), 2.16 (s, 3H, ArCH$_3$), 1.96-1.88 (m, 1H, bornyl H-6 endo), 1.80-1.72 (m, 1H, bornyl H-5 exo), 1.71-1.67 ((bt, 1H, $^3J$=4.40 Hz, bornyl H-4), 1.37-1.29 (m, 1H, bornyl H-6 exo), 1.22-1.18 (m, 7H, bornyl H-5endo and ArCH(CH̲$_3$)$_2$), 1.03 (d, 3H, $^3J$=6.85 Hz, CH̲$_3$(CH$_3$)CHCH(NH)CO), 1.01-0.93 (m, 1H, bornyl H-3 endo), 0.95 (d, 3H, $^3J$=6.95 Hz, CH$_3$(CH̲$_3$)CHCH(NH)CO), 0.89 (s, 3H, bornyl C-7 CH$_3$), 0.87 (s, 3H, bornyl C-7 CH$_3$) and 0.84 (s, 3H, bornyl C-1 CH$_3$).

9) NDH 4648

$^1$HNMR (CDCl$_3$) δ7.09 (d, 1H, $^3J$=7.75 Hz, ArH-2), 6.97 (dd, 1H, $^3J$=7.75 Hz, $^4J$=1.45 Hz, ArH-3), 6.90 (s, 1H, ArH-5), 5.54 (d, 1H, $^3J$=9.15 Hz, NH), 5.35 (bt, 1H, OCH$_2$—CH̲=), 5.12-5.04 (m, 2H, 2 vinyl protons), 4.75-4.61 (m, 2H, OCH̲$_2$—CH=), 4.38-4.32 (dd, 1H, $^3J$=9.18 Hz and $^3J$=4.58 Hz, CH̲—CO), 2.89-2.86 (septet, 1H, $^3J$=6.86 Hz, ArCH̲(CH$_3$)$_2$), 2.28-2.18 (m, 1H, (CH$_3$)$_2$CH̲CH(NH)CO), 2.15 (s, 3H, ArCH$_3$), 2.14-1.93 (m, 8H, 4 CH$_2$ units of farnesyl moiety), 1.71 (s, 3H, O—CH$_2$CH=C(CH̲$_3$)—), 1.66 (s, 3H, CH$_2$CH$_2$C=C(CH̲$_3$)CH$_2$—), 1.58 (s, 6H, C=C(CH̲$_3$)$_2$), 1.20 (d, 6H, $^3J$=6.95 Hz, ArCH(CH̲$_3$)$_2$), 1.00 (d, 3H, $^3J$=6.85 Hz, CH̲$_3$(CH$_3$)CHCH(NH)CO) and 0.92 (d, 3H, $^3J$=6.9 Hz, CH$_3$(CH̲$_3$)CHCH(NH)CO).

Examples of Aspect II

Synergism of anti-inflammatory responses by anti-inflammatory agents covalently coupled to amino acids (Aspect II) was demonstrated by preparation of the S-naproxen-valine conjugate, and screening it in the MEVM against CEES challenge. MEVM is a standard in vivo assay for assessment of anti-inflammatory potential in addressing chemically-induced injury to rodent skin. CEES is one of the inflammation inducers employed in the MEVM assay. A compound of the invention, Formula (IV-acid) (NDH 4476) provided four times better inflammation suppression (44%) than naproxen itself under the same conditions. The corresponding ethyl ester analog (IV-ethyl ester) (NDH 4535) was equipotent but the 3,3-dimethylbutyl ester (IV-3,3-dimethylbutyl-) (NDH 4596) was superior at 52% inflammation suppression. The latter molecule also was an inhibitor of AChE displaying anti-cholinergic activity with an IC$_{50}$ of 18.6 µM.

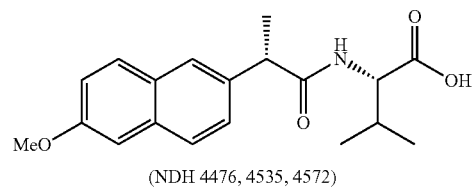

(IV-acid and IV-esters)

(NDH 4476, 4535, 4572)

The phenylalanine conjugate of S-naproxen (esterified as the 3,3-dimethylbutyl ester) shown in Formula (V) (NDH 4572) displayed an impressive 83% suppression of CEES-induced inflammation while S-naproxen itself yielded a mere 11% suppression of CEES inflammation. The six-carbon ester not only adds lipophilicity and promotes solubility of the NSAID-amino acid pharmaceutical in ointment excipients, but through its action as a bioisostere of choline it provides anticholinergic activity. For a discussion of how anticholinergic activity can facilitate anti-inflammatory responses see S. C. Young et al, Investigation of anticholinergic and non-steroidal anti-inflammatory prodrugs which reduce chemically-induced skin inflammation, *J. Appl. Tox.*, 2012, 32: 135-141. The choline bioisostere 3,3-dimethylbutyl alcohol provides cholinesterase inhibition in the final anti-inflammatory drug-amino acid-choline bioisostere construct. For the naproxen-phenylalanine platform, Formula (V), (also known as NDH 4572) this choline mimic generates an IC$_{50}$ value of 4.7 µM against AChE.

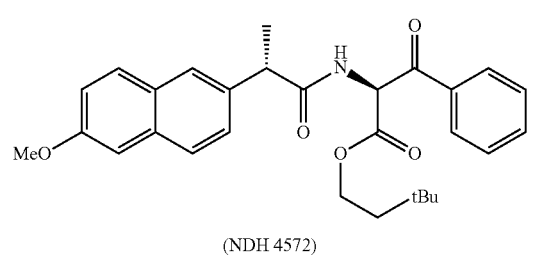

(V)

(NDH 4572)

The phenylalanine conjugate of the NSAID diclofenac (esterified as the 3,3-dimethylbutyl ester; Formula (VI)) (NDH 4578) displayed a complete (100%) suppression of induced inflammation in the mouse. In the same assay diclofenac itself displayed a mere 17% suppression of inflammation.

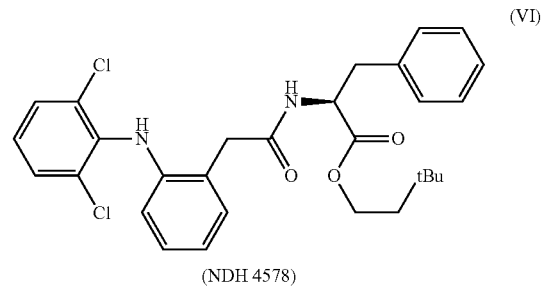 [SMILES: CC(C)(C)CCOC(=O)[C@H](Cc1ccccc1)NC(=O)Cc1ccccc1Nc1c(Cl)cccc1Cl]

(VI)

(NDH 4578)

Despite the fact that it is an NSAID, topical ibuprofen by itself was found to be a dermal irritant, adding 11% additional inflammation to CEES-induced injury.

Furthermore, vanillylamine is only a weak anti-inflammatory; however, the triple conjugate of ibuprofen, vanillylamine, and valine, Formula (VII) (NDH 4479), provided a 94% suppression of CEES-induced inflammation.

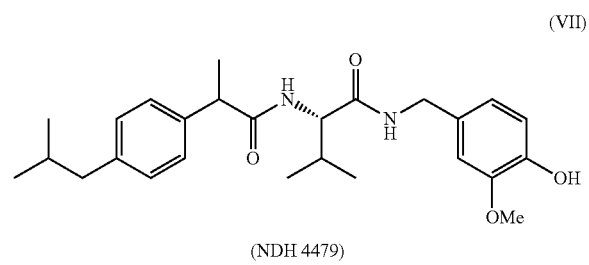 [SMILES: COc1cc(CNC(=O)[C@@H](NC(=O)C(C)c2ccc(CC(C)C)cc2)C(C)C)ccc1O]

(VII)

(NDH 4479)

Aspect II: Design and Synthesis of the NSAID-Amino Acid Conjugates and NSAID-Amino Acid—Anticholinergic Conjugates The NSAID-amino acid conjugates (as esters or as free carboxylic acids) were synthesized by the following general method. All NSAIDs employed herein bear a pendant carboxylic acid group. To illustrate how such molecules are linked to the amino acid carrier the designation NSAID-CO— is used to convey that the fundamental ring system of the NSAID is attached through its carboxyl moiety. The required amino acids (0.60 mmol) were first esterified with ethyl alcohol, n-butyl alcohol, or 3,3-dimethylbutyl alcohol in toluene with p-toluenesulfonic acid as a catalyst. The amino acid esters could be isolated. crystallized, and purified in 55-85% yields if so desired. Then the requisite NSAID (0.60 mmol), and HOBt (0.66 mmol) were added in $CH_2Cl_2$ (5 mL) under a nitrogen atmosphere. The reaction contents were stirred at room temperature for 15 min, until the solution became clear. EDC.HCl (1.1 equiv., 126 mg, 0.66 mmol) was then added and the reaction contents were stirred at room temperature overnight (16 hr). Distilled water was added and the organic layer was separated. The aqueous phase was then extracted with methylene chloride (25 mL) and the two organic layers were combined and washed with 1 M HCl (2×50 mL), saturated $NaHCO_3$ (50 mL), and brine. The organic layer was then dried over anhydrous $MgSO_4$, filtered, and concentrated to yield the final product, which was purified via column chromatography using a gradient separation with hexanes (100 to 50%) and ethyl acetate (0 to 50%) as the eluting solvent mixture. Yields on the amide-forming step were 89-99% and after column chromatography were homogeneous by TLC. These NSAID-amino acid—ester conjugates were sufficiently pure for in vitro (AChE) screening or in vivo (MEVM) testing. Hydrolysis of these esters in 1:1 water:THF with 1 mmol of $Na_2CO_3$ could free the carboxylic acids (giving the simple NSAID-amino acid conjugate if so desired) in 40% yield. Products were identified by exact mass spectrometry with experimental values within +/−0.02 amu of the theoretical mass. In this fashion, on the valine platform, (IV-ethyl ester, NDH 4535) (white solid, mp 135-139° C.) and (IV-3,3-dimethylbutyl ester, NDH 4596) (clear oil Rf=0.30 with 4:1 hexane:ethyl acetate) and (IV-free acid, NDH 4476) (white solid, 164-166° C.) were prepared. While this method is suitable for any NSAID-amino acid or NSAID-amino acid ester, the specific products prepared by this route were NDH 4651, NDH 4652, NDH 4653, and NDH 4654. Scheme I illustrates this pathway with any alcohol (R'—OH) and any carboxyl-bearing NSAID but the method has been specifically applied to these alcohols: ethanol, n-butanol, 3,3-dimethylbutyl alcohol, 2-(trimethylsilyl)ethyl alcohol, and to these NSAIDs: ibuprofen, naproxen, indomethacin, and diclofenac.

Scheme I

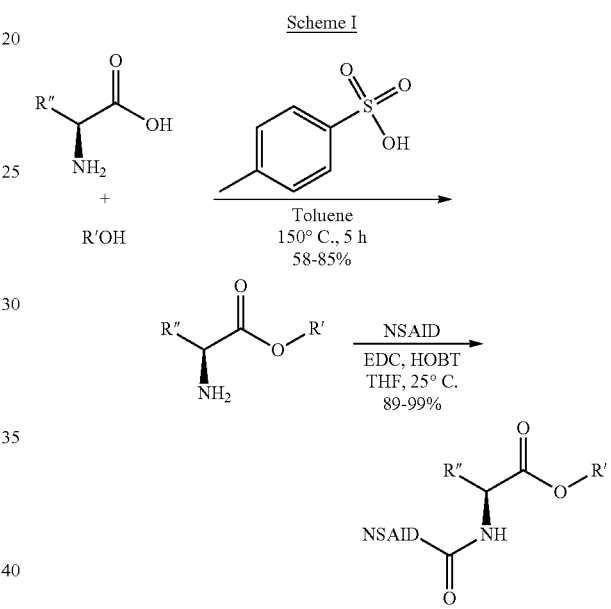

For the proline conjugates, two structurally-related products were observed via nuclear magnetic resonance (NMR) spectroscopy, even following extensive chromatographic purification. In all cases, the percentage of the second product ranged from 13 to 19%, depending on the NSAID. The final products were homogeneous by TLC. It was determined that the sterically hindered proline amide bond undergoes cis-trans isomerization (Scheme II) which can be detected via NMR (vide infra). Cis-trans isomerization of the proline peptide bond is well documented and plays an important role in protein folding.

Scheme II

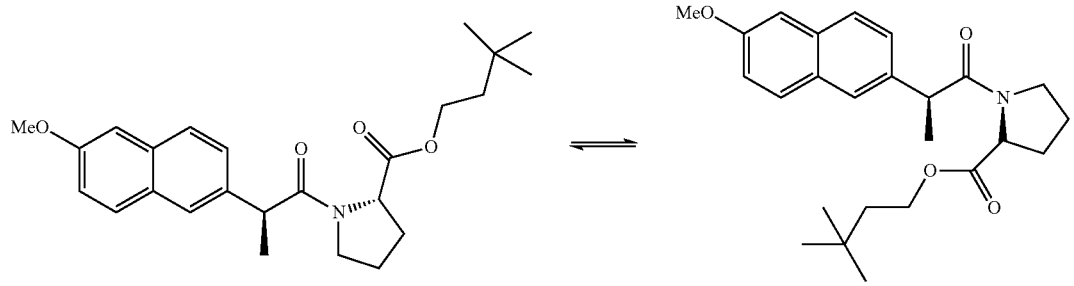

Aspect II: Design and Syntheses of Amino Acid Conjugates Requiring Specialized Transformations A. Preparation of Amino Acid Conjugates which Include a Ketone Body (3-Hydroxybutyrate) Illustrated with NDH 4571 as an Example The labile 3-hydroxy group requires protection before it can be linked to an amino acid platform. For this the TBDMS-protected 3-hydroxybutyric acid ((R)-3-[(tert-butyl)dimethylsilyloxy]butanoic acid) was first prepared according to the procedure of D. Seebach, et. al. (Helvetica Chimica Acta, 79(3), 670 (1996)) and used as the starting material. Seebach's protected acid compound was subsequently converted to the thiazolide of the silyl-protected butanoic acid, first structure shown in Scheme III. The protected acid (1.776 g, 8.133 mmol), mercaptothiazoline (970 mg 8.133 mmol), and N,N'-dicyclohexylcarbodiimide (DCC) (1.762 g, 1.05×8.133 mmol) were dissolved in 40 mL of $CH_2Cl_2$. The flask was immersed in an ice bath, and after sufficient chilling, a catalytic amount of 4-dimethylaminopyridine (DMAP) was added. The ice bath was removed stirring for 2 h, and the mixture was stirred at room temperature for an additional 2 h. The urea was filtered off, and the filtrate extracted with saturated $NaHCO_3$, 1N HCl and saturated NaCl. The organic layer was dried over $MgSO_4$, filtered and concentrated. A portion of the crude (850 mg) was purified by column chromatography on silica gel (70 g) eluting with hexanes/ethyl acetate. 8:2 to give a 78% yield of a bright yellow oil, $R_f$=0.49.

droxy-3-methoxybenzylamine hydrochloride, also known as vanillylamine hydrochloride, (144 mg, 1.05×0.723 mmol) and $NEt_3$ (77 mg, 106 μL, 1.05×0.723 mmol) were dissolved in $CH_2Cl_2$ (7 mL). The solution was stirred and chilled in an ice bath. To the cold mixture was added EDC (153 mg, 1.1×0.723 mmol). The mixture was allowed to stir to room temperature overnight. The mixture was diluted with $CH_2Cl_2$ and extracted with water, 1N HCl, saturated $NaHCO_3$, and saturated NaCl The organic layer was dried over Mg $SO_4$, filtered and concentrated. The crude product was purified by column chromatography on silica gel (50 g) eluting with $CH_2Cl_2$/MeOH, 94:6 (v/v), $R_f$=0.40, to give a 70% yield. Although Scheme II, Step 2 shows the incorporation of vanillylamine, any nucleophilic anti-inflammatory could be used (e.g., a phenolic-protected vanillyl alcohol).

In Step 3, the silyl-protected conjugate (229 mg, 0.506 mmol) was desilylated by dissolving in 5 mL of MeOH, adding $NH_4F$ (94 mg, 5×0.506 mmol) and heating at 60° C. for 7 days. The solution was cooled to room temperature and concentrated under reduced pressure. The crude product was purified by column Chromatography on silica gel (40 g) eluting with $CH_2Cl_2$/MeOH 98:2 (v/v) and increasing to 92:8 to give a yield of 84%, ($R_f$=0.23 ($CH_2Cl_2$/MeOH, 94:6 (v/v), mp=164-174° C. with rapid heating). Spectral evidence confirmed the structure of NDH 4571. $^1$H NMR (acetone $d_6$) δ: 7.70-7.64 (m, 1H, —NH— of valine), 7.44 (d, 1H, $^3J$=4.5 Hz, $CH_3CH(OH)$—), 6.90 (m, 1H, Ar), 6.74-6.69 (m, 2H, Ar), 4.31-4.25 (m, 3H, —$NCH(CH_3)_2$—

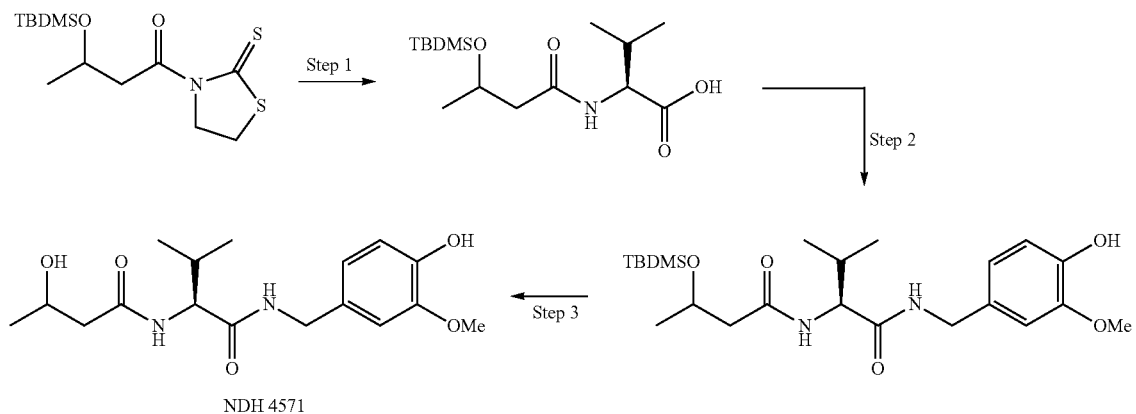

Scheme III

NDH 4571

While Step 1 can employ any of the anti-inflammatory amino acids, the pathway is illustrated with L-valine. The thiazolide (331.9 mg, 1.038 mmol), L-valine (128 mg, 1.05×1.038 mmol) and diisopropylethylamine (268 mg, 362 μL, 2×1.038 mmol) were dissolved in a mixture of 5.2 mL each of water and THF. The reaction mixture was stirred vigorously overnight. The colorless mixture was diluted with $CH_2Cl_2$ and extracted with 1 N HCl. The organic layer was concentrated, and the residue was dissolved in ether. The ether solution was extracted with saturated $NaHCO_3$. The bicarbonate layer was extracted twice with ether and then carefully acidified to pH=1 using 4N HCl. The resulting aqueous mixture was extracted with $CH_2Cl_2$. The organic layer was dried over $MgSO_4$, filtered, and concentrated. This product of Step 1 was used in Step 2 without further purification.

In Step 2, the N-substituted valine derivative (229.6 mg, 0.723 mmol), HOBt (103 mg, 1.05×0.723 mmol), 4-hyand Ar—$CH_2$—), 4.09-4.03 (m, 1H, $CH_3CH(OH)$—), 3.80 (s, 3H, Ar—$OCH_3$). 2.42-2.27 (m, 2H, —C(H(OH)C $H_2$CO—), 2.20-2.07 (m, 1H, —$CH(CH_3)_2$—), 1.14-1.11 (m, 3H, —$CH(CH_3)_2$), 0.93 (t, 3H, $^3J$=6.80 Hz, $CH(CH_3)_2$) and 0.91-0.88 (2 sets of doublets, 3H, $^3J$=6.85 Hz each, C $H_3CH(OH)$—).

B. Preparation of NSAID-Amino Acid Conjugates with Free Amino Acid Carboxyls (Illustrated with NDH 4476 or Compound IV-Acid)

While the amino acid conjugates of NSAIDs (those with a free amino acid carboxyl) can be prepared by hydrolysis of the ester products of Scheme I, a far better route involves the thiazolide pathway. Thus, the synthesis of IV-acid was carried out as described in step 1 for the synthesis of NDH 4571 using the thiazolide of (S)-naproxen being condensed with L-valine to render a 68% yield of a white solid. NDH 4476 or IV-acid. Mp=164-166° C.: $R_f$=0.56 (rocket), $CH_2Cl_2$/MeOH, 9:1 (v/v); Exact mass (ESI) Calculated for $C_{19}H_{24}NO_4$ [M+H]330.1700. found 330.1680. $^1$H NMR (CDCl$_3$) δ: 7.72-7.76 (m, 3H, Ar), 7.36 (d, 1H, $^3$J=8.40 Hz), 7.14 (dd, 1H. $^3$J=8.95 Hz, $^4$J=2.3 Hz), 7.10 (s, 1H), 5.82 (d, 1H, $^3$J=8.35 Hz), 4.45-4.42 (m, 1H), 3.90 (s, 3H), 3.77 (q, 1H, $^3$J=7.15 Hz), 2.16-2.09 (m, 1H), 1.60 (d, 3H, $^3$J=7.25 Hz), 0.87 (d, 3H, $^3$J=6.85 Hz) and 0.74 (d, 3H, $^3$J=6.85 Hz).

Although illustrated herein with S-naproxen and L-valine, this thiazolide route can be used for any carboxyl-terminated NSAID and any amino acid co-reactant.

C. Preparation of a Formula II Example Wherein and NSAID and a Vanilloid are Linked to an Amino Acid Through Nitrogen Atoms, Illustrated with NDH 4479 (Compound VII)

Compound VII or NDH 4479 is one of the most potent anti-inflammatories observed in the MEVM, with 110% suppression of phorbol-induced and 94% suppression of CEES-induced inflammation. The synthesis of VII was carried out as described in steps 1 and 2 for the synthesis of NDH 4571 but using the thiazolide of ibuprofen to give a 72% yield of a solid. Mp=56-66° C. with rapid heating; purification by column chromatography with silica gel and CH$_2$Cl$_2$/acetone, 92:8 (v/v); R$_f$=0.23, CH$_2$Cl$_2$/acetone, 92:8 (v/v); Exact mass (ESI) Calculated for $C_2H_{37}N_2O_4$ [M+H] 441.2748. found 441.2742. $^1$H NMR (CDCl$_3$) δ: 7.17-7.03 (m, 4H, Ar of Ibuprofen). 6.85-6.64 (m, 3H, Ar of vanillamine). 6.25-6.06 (m, 1H, NH of valine), 5.86-5.76 (m, 1H, NH of vanillamine), 5.57 (br s, 1H, ArOH), 4.40-4.08 (m, 3H, —NCHCO— and Ar—CH$_2$—), 3.84-3.82 (m, 3H, ArOCH$_3$), 3.59-3.49 (m, 1H, ArCH(CH$_3$)CO—), 2.45-2.40 (m, 2H, (CH$_3$)$_2$CHCH$_2$—), 2.12-1.95 (m, 1H, (CH$_3$)$_2$C HCH$_2$—), 1.85-1.76 (m, 1H, (CH$_3$)$_2$CHCH(NH)CO—), 1.49-1.43 (m, 3H, ArCH(CH$_3$)CO—) and 0.88=0.63 (m, 12H, (CH$_3$)$_2$CHCH$_2$— and (CH$_3$)$_2$CHCH(NH)CO—).

D. Alternative Preparation of NDH 4535

While the synthesis of NDH 4535 could be achieved as described in Scheme I with ethanol as the esterifying alcohol, a much higher yield can be achieved by the thiazolide route. The synthesis of NDH 4535 is best carried out as described in step 1 for the synthesis of NDH 4571 using the thiazolide of (S)-naproxen, L-valine ethyl ester hydrochloride and THF only as solvent. The product was purified by column chromatography on silica gel and eluting with hexanes/ethyl acetate, 7:3 (v/v) to yield 84% of a crystalline product: mp=100-102° C., R$_f$=0.43 (hexanes/ethyl acetate 7:3 (v/v)). Exact mass (ESI) Calculated for $C_{21}H_{28}NO_4$ [M+H]358.2013. found 358.2021. $^1$H NMR (CDCl$_3$) δ: 7.73-7.68 (m, 3H, Ar), 7.38 (dd, 1H, $^3$J=8.5 Hz, $^4$J=1.8 Hz, Ar), 7.13 (dd, 1H, $^3$J=8.9 Hz, $^4$J=2.55 Hz, Ar), 7.10 (d, 1H, $^4$J=2.45 Hz, Ar), 4.50-4.46 (m, 1H, N—CHCO), 4.14-4.01 (m, 2H, OCH$_2$CH$_3$), 2.10-2.03 (m, 1H, —CH(CH$_3$)$_2$), 1.60 (d, 3H, $^3$J=7.2 Hz, —CH(CH$_3$)CO—), 1.15 (t, 3H, $^3$J=7.15 Hz, OCH$_2$CH$_3$), 0.85 (d, 3H, $^3$J=6.85 Hz, —CH(CH$_3$)$_2$) and 0.74 (d, 3H, $^3$J=6.85 Hz, —CH(CH$_3$)$_2$).

E. Preparation of a Mixed Vanilloid-Amino Acid Platform Illustrated with NDH 4483

Since both vanillylamine and vanillyl alcohol possess anti-inflammatory activities and in similar fashion to the amino acid valine, the triple combination consistently displays MEVM numbers >65%. The synthesis of NDH 4483 was carried out as described in steps 1 and 2 for the synthesis of NDH 4571 but using the thiazolide carbamate of 4-acetoxy-3-methoxyvanillyl alcohol. The product was purified by column chromatography on silica gel and eluting with CH$_2$Cl$_2$MeOH, 94:6 (v/v) to give a 61% yield of a white solid: R$_f$=0.53 (CH$_2$Cl$_2$/MeOH, 92:8 (v/v). Exact mass (ESI) Calculated for $C_{24}H_{31}N_2O_4$ [M+H]475.2075. found 475.2058.

$^1$H NMR (CDCl$_3$) δ: 6.97 (d, 1H, $^3$J=8.0 Hz, H-5 of vanillyl alcohol), 6.92 (s, 1H, H-2 of vanillyl alcohol), 6.88 (d, 1H, $^3$J=8.2 Hz, H-6 of vanillyl alcohol), 6.82 (d, 1H, $^3$J=8.0 Hz, H-5 of vanillylamine). 6.75 (s, 1H, H-2 of vanillylamine), 6.72 (d, 1H, $^3$J=7.9 Hz, H-6 of vanillylamine), 5.61 (s, 1H, ArOH), 5.34 (d, 1H, $^3$J=8.5 Hz, NH of valine), 5.05-4.99 (m, 2H, ArCH$_2$O —), 4.41-4.27 (m, 2H, ArCH$_2$NH—), 3.96-3.91 (m, 1H, —NHCHCO—), 3.82 (s, 3H, ArOCH$_3$), 3.80 (s, 3H, ArOCH$_3$), 2.29 (s, 3H, ArOCOC H$_3$), 2.13 (m 1H, —CH(CH$_3$)$_2$), 0.97 (d, 3H, $^3$J=6.8 Hz, —CH(CH$_3$)CH$_2$) and 0.91 (d, 3H, $^3$J=6.8 Hz, —CH(C H$_3$)CH$_3$).

The amino acid—3,3-dimethylbutyl esters lacking the NSAID moiety were all inactive in inhibition of AChE as were the NSAID-amino acid ethyl and n-butyl esters. These displayed IC$_{50}$ values greater than 100 μM and precise IC$_{50}$ values could not be determined due to solubility limitations of the compound being tested. Some of these simple conjugates did, however, possessed modest (usually 5- 44%) anti-inflammatory activity in the mouse ear vesicant model (e.g., IV-acid and IV-ethyl ester at 40-44% and the n-butyl esters designated NDH 4651-4654 at <25%). These data indicate that the choline mimics alone (or AA linked choline mimics) do not have a high affinity for AChE. Low micromolar anticholinesterase IC$_{50}$ activities are obtained only when the choline mimics are covalently linked to an aromatic and lipophilic NSAID such as diclofenac. While the relationship between the IC$_{50}$ values for inhibition of AChE and the measured anti-inflammatory effects in the MEVM is not linear, it can be observed (Table I) that compounds with the lowest IC$_{50}$'s (e.g., below 3.3 micromolar) displayed superior inflammation suppression percentages for at least one of the inflammation-inducers. (See NDH 4537, 4577, 4578, and 4591)

TABLE I

NSAID-Amino Acid - 3,3-dimethylbutyl Esters (other structural examples are described elsewhere herein)

| NDH # | NSAID | Amino Acid | AChE IC$_{50}$ (μM) | % CEES$^a$ | % TPA$^a$ |
|---|---|---|---|---|---|
| 4618 | Naproxen | Proline | >100* | 34 | Irritant |
| 4619 | Ibuprofen | Proline | NT | 24 | 35 |
| 4617 | Indomethacin | Proline | >25* | 25 | 68*** |
| 4628 | Diclofenac | Proline | 15.4 +/- 0.1 | 10 | 76*** |
| 4614 | Ibuprofen | Glycine | 27.9 +/- 2.7 | Irritant | 18 |
| 4613 | Naproxen | Glycine | NT | 66** | 54** |
| 4615 | Indomethacin | Glycine | 6.63 +/- 0.4 | 21 | 55** |
| 4627 | Diclofenac | Glycine | >50* | Irritant | 45** |
| 4576 | Ibuprofen | Phenyl-alanine | 4.34 +/- 0.2 | Irritant | Irritant |
| 4572 | Naproxen | Phenyl-alanine | 4.77 +/- 0.2 | 83** | 42** |
| 4577 | Indomethacin | Phenyl-alanine | 2.55 +/- 0.7 | 62** | 79** |
| 4578 | Diclofenac | Phenyl-alanine | 1.31 +/- 0.1 | 120** | 90** |
| 4595 | Ibuprofen | Valine | 8.91 +/- 0.4 | 47 | Irritant |
| 4596 | Naproxen | Valine | 18.6 +/- 3.0 | 51 | 22 |
| 4537 | Indomethacin | Valine | 3.29 +/- 0.3 | 59 | 107*** |
| 4591 | Diclofenac | Valine | 1.85 +/- 0.1 | 85** | 31 |

*A precise IC$_{50}$ could not be determined due to limits in inhibitor solubility
NT means not tested
$^a$Values differ from a positive control based on one-way ANOVA,
**P < 0.05,
***P < 0.005

Representative Physical Data for Anti-Inflammatories of Aspect II Containing Amino Acid Linkers Stability. If vanillyl amine (i.e., 3-methoxy-4-hydroxybenzyl-NH—) is attached to any of these anti-inflammatory amino acid platforms it constitutes a shelf-stable, slowly metabolized moiety. However, if vanillyl alcohol (i.e., 3-methoxy-4-hydroxybenzyl-O—) is attached, the resulting candidate pharmaceuticals are unstable unless the free-phenolic hydroxyl is protected by acylation. Acetate is a preferred protecting group and the derived products are suitable therapeutic candidates.

(S)-3,3-Dimethylbutylpyrrolidine-2-carboxylate

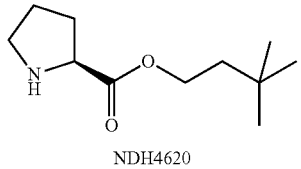

NDH4620

Light yellow liquid, 85% yield; $R_f$ 0.12 (Hexanes:ethyl acetate 1:1): $^1$H NMR (500 MHz, CDCl$_3$)=δ 0.92 (s, 9H), 1.53-1.57 (t, 2H, J=7.15 Hz), 1.70-1.76 (m, 2H), 1.79-1.84 (m, 1H), 270, 2.05-2.11 (m, 1H), 2.85-2.90 (m, 1H), 3.03-3.08 (m, 1H), 3.69-3.72 (dd, 1H, J=5.70, 8.60 Hz), 4.14-4.17 (dt, 2H, J=1.70, 3.70 Hz); $^{13}$C NMR (125 MHz, CDCl$_3$): δ25.5, 29.6, 29.7, 30.3, 41.8, 47.1, 59.9, 62.7, 175.6; HRMS (m/z): calc. for C$_{11}$H$_{21}$NO$_2$ 200.1645; meas. 200.1638.

(S)-3,3-Dimethylbutyl-1-(2-(4-isobutylphenyl)propanoyl)pyrrolidine-2-carboxylate

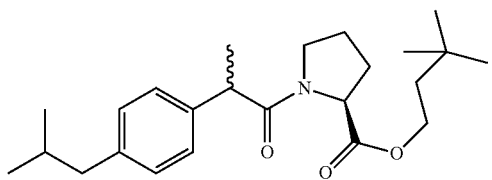

NDH4619

Clear liquid, 93% yield; $R_f$ 0.74 (Hexanes:ethyl acetate 1:1); according to $^1$H NMR, 19.2% of the cis isomer of the proline peptide bond is present: $^1$H NMR trans isomer (500 MHz, CDCl$_3$): δ 0.85-0.89 (m, 6H), 0.92 (s, 9H), 1.38-1.42 (q, 3H, J=10.9 Hz), 1.54-1.57 (t, 2H, J=7.55 Hz), 1.69-1.90 (m, 4H), 1.93-2.02 (m, 1H), 2.38-2.42 (dd, 2H, J=2.55, 7.18 Hz), 3.17-3.50 (m, 2H), 3.64-3.76 (m, 1H), 4.10-4.20 (m, 2H), 4.39-4.49 (m, 1H), 7.02-7.08 (m, 2H), 7.13-7.19 (m, 2H); cis isomer: δ0.85-0.89 (m, 6H), 0.87 (s, 9H), 1.38-1.42 (q, 3H, J=10.9 Hz), 1.47-1.50 (t, 2H, J=7.50 Hz), 1.69-1.90 (m, 4H), 2.05-2.15 (m, 1H), 2.38-2.42 (dd, 2H, J=2.55, 7.18 Hz), 3.173.50 (m, 2H), 3.64-3.76 (m, 1H), 4.10-4.15 (m, 1H), 4.21-4.25 (m, 1H), 4.39-4.53 (m, 1H), 7.027.08 (m, 2H), 7.13-7.19 (m, 2H); $^{13}$C NMR trans isomer (125 MHz, CDCl$_3$): δ20.3, 22.4, 22.5, 24.9, 29.6, 29.8, 30.1, 41.6, 44.5, 45.1, 46.8, 59.2, 62.7, 127.3, 129.4, 138.4, 140.0, 172.3, 172.6; cis isomer: δ 20.4, 22.3, 22.5, 24.8 29.0, 30.2, 31.2, 41.7, 44.6, 45.0, 46.7, 58.9, 62.8, 127.0, 127.3, 129.5, 129.6, 172.8, 172.9; Calc. for C$_{24}$H$_{37}$NO$_3$.0.25H$_2$O (392.06): C, 73.53; H, 9.64; N, 3.57. Found: C, 73.86; H, 9.41: N, 3.47.

(S)-3,3-Dimethylbutyl-1-((S)-2-(6-methoxynaphthalen-2-yl)propanoyl)pyrrolidine-2-carboxylate

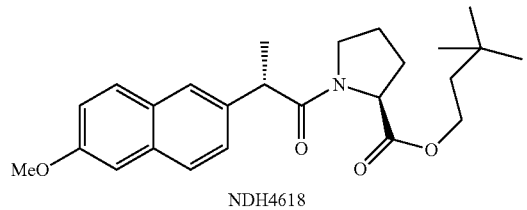 [SMILES: COc1ccc2cc([C@H](C)C(=O)N3CCC[C@H]3C(=O)OCCC(C)(C)C)ccc2c1]

NDH4618

White solid, 73% yield; MP 111.5-112.5° C.; $R_f$ 0.62 (Hexanes:ethyl acetate 1:1); according to $^1$H NMR, 13.4% of the cis isomer of the proline peptide bond is present: $^1$H NMR, trans isomer (500 MHz, DMF): δ0.99 (s, 9H), 1.52-1.57 (m, 5H). 1.92-1.97 (m, 2H), 2.04-2.07 (m, 1H), 2.332.36 (m, 1H), 3.35-3.39 (m, 1H), 3.87-3.92 (m, 1H), 4.07 (s, 3H), 4.17-4.26 (m, 3H), 4.55-4.57 (dd, 1H, J=4.20, 8.60 Hz), 7.31-7.34 (dd, 1H, J=2.50, 9.00 Hz), 7.50 (d, 1H, J=2.50 Hz), 7.61-7.64 (dd, 1H, J=1.75, 8.45 Hz), 7.94-7.98 (t, 3H, J=8.65 Hz); cis isomer: δ 1.12 (s, 9H), 1.52-1.57 (m, 5H), 1.76-1.80 (t, 2H, J=7.25 Hz), 1.92-1.97 (m, 2H), 1.91-1.97 (m, 1H), 2.19-2.23 (m, 1H), 3.55-3.60 (m, 1H), 3.87-3.92 (m, 1H), 4.07 (5, 3H), 4.43-4.45 (m, 2H), 7.31-7.34 (dd, 1H, J=2.50, 9.00 Hz), 7.50 (d, 1H, J=2.50 Hz), 7.61-7.64 (dd, 1H, J=1.75, 8.45 Hz), 7.91 (bs, 1H). 7.94-7.98 (l, 2H, J=8.65 Hz); $^{13}$C NMR, trans isomer (125 MHz, DMF): δ20.1, 22.4, 31.1, 24.9, 41.7, 44.0, 46.9, 55.2, 59.4, 62.1, 63.2, 106.1, 118.9, 126.3, 126.9, 127.4, 129.3, 129.4, 133.9, 137.3, 157.9, 172.0, 172.4: cis isomer: δ 20.1, 22.4, 31.1, 41.8, 44.3, 46.6, 55.2, 59.2, 62.1, 63.2, 106.0, 119.1, 125.9, 126.3, 126.9, 127.6, 129.3, 129.4, 134.0, 137.1, 157.9, 172.5, 172.8; Calc. for C$_{25}$H$_{33}$NO$_4$ (411.53): C. 72.96; H, 8.08; N, 3.40. Found: C, 73.22: H, 7.98; N, 3.47.

(S)-3,3-Dimethylbutyl-1-(2-(1-(4-Chlorobenzoyl)-5-methoxy-2-methyl-1H-indol-3-yl)acetyl) pyrrolidine-2-carboxylate

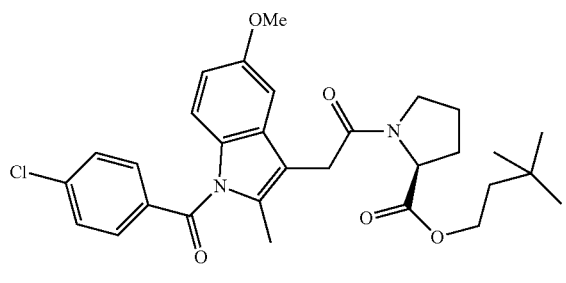

NDH4617

Yellow oil, 96% yield; $R_f$ 0.47 (Hexanes:ethyl acetate 1:1); according to $^1$H NMR, 18.5% of the cis isomer of the proline peptide bond is present: $^1$H NMR, trans isomer (500 MHz, CDCl$_3$): δ 0.88 (5, 9H), 1.41-1.45 (l, 2H, J=7.55 Hz), 1.93-2.03 (m, 2H), 2.05-2.09 (m, 1H), 2.18-2.20 (m, 1H), 2.36 (5, 3H), 3.62-3.71 (m, 2H), 3.70 (5, 2H), 3.77 (5, 3H), 4.03-4.07 (m, 21H), 4.30-4.33 (dd, 1H, J=4.55, 8.60 Hz), 6.63-6.66 (dd, 1H, J=2.50, 9.00 Hz), 6.94-6.97 (m, 1H), 6.99 (d, 1H, J=2.50 Hz), 7.52 (d, 2H, J=8.45 Hz), 7.61-7.64 (m, 2H): cis isomer: δ 0.89 (5, 9H), 1.47-1.51 (l, 2H, J=7.40 Hz), 1.84-1.90 (m, 1H), 1.93-2.03 (m, 2H), 2.21 (5, 3H), 3.45-3.49 (n, 3H), 3.70 (5, 21H), 3.77 (s, 31H), 4.08-4.13 (m, 2H), 4.58-4.61 (dd, 1H, J=1.95, 8.60 Hz), 6.63-6.66 (dd, 1H, J=2.50.9.00 Hz), 6.94-6.97 (m, 1H), 6.99 (d, 1H, J=2.50 Hz), 7.52 (d, 2H, J=8.45 Hz), 7.61-7.64 (m, 2H): $^{13}$C NMR, trans isomer (500 MHz, CDCl$_3$): 0 13.6, 25.0, 29.5, 29.6, 29.7, 31.2, 41.6, 47.3, 55.7, 59.3, 62.9, 101.7, 111.6, 112.9, 114.8, 129.1, 130.8, 130.9, 131.2, 134.0.135.6, 139.2, 156.0, 168.3, 168.8, 172.3: cis isomer: 6 13.5, 22.3, 25.0, 29.1, 29.7, 31.7, 41.7, 46.8, 53.5, 59.6, 63.5, 101.6, 111.7, 112.9, 114.8, 129.1, 130.8, 130.9, 131.2, 134.0, 135.6, 139.2, 156.1, 168.3, 168.9, 172.3: Calc. for C$_{30}$H$_{35}$ClN$_2$O$_5$.0.5CH$_2$Cl$_2$ (581.53): C, 63.00; H, 6.24; N, 4.82. Found: C, 63.34; H, 5.69: N, 4.81.

(S)-3,3-Dimethylbutyl-1-(2-(2-(2,6-dichlorophenylamino)phenyl)acetyl)pyrrolidine-2-carboxylate

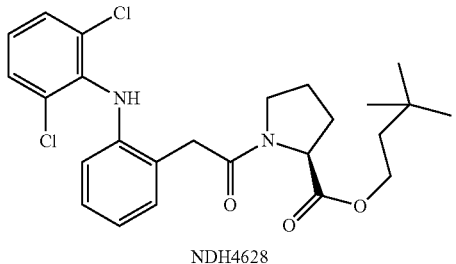 [SMILES: CC(C)(C)CCOC(=O)[C@@H]1CCCN1C(=O)Cc1ccccc1Nc1c(Cl)cccc1Cl]

NDH4628

Clear oil, 82% yield; R$_f$ 0.31 (Hexanes:ethyl acetate, 4:1); according to $^1$H NMR, 22.1% of the cis isomer of the proline peptide bond is present: $^1$H NMR, trans isomer (500 MHz, CDCl$_3$): δ 0.86 (s, 9H), 1.41-1.45 (l, 2H, J=15.0 Hz), 1.99-2.01 (m, 2H), 2.05-2.11 (m, 1H), 2.11-2.17 (m, 1H), 3.62-3.71 (m, 2H), 3.72-3.87 (m, 3H), 4.06-4.14 (m, 2H), 4.48-4.51 (dd, 1H, J=3.50, 8.60 Hz), 6.48 (d, 1H, J=7.75 Hz), 6.84-6.89 (l, 1H, J=7.25 Hz), 6.91-6.94 (l, 1H, J=8.00 Hz), 7.06 (d, 1H, J=7.40 Hz), 7.15 (d, 1H, J=7.50 Hz), 7.29 (d, 2H., J=8.00 Hz); $^1$H NMR, cis isomer (500 MHz, CDCl$_3$): δ 0.90 (s, 9H), 1.52-1.56 (l, 2H, J=7.45 Hz), 1.88-1.94 (m, 2H), 2.13-2.19 (m, 1H), 2.23-2.32 (m, 1H), 3.54-3.62 (m, 2H), 3.72-3.87 (m, 3H), 4.18-4.28 (m, 2H), 4.63-4.66 (dd, 1H, J=2.55, 8-.53 Hz), 6.49-6.51 (m, 1H), 6.85-6.88 (m, 1H), 6.91-6.95 (l, 1H, J=8.00 Hz), 7.04-7.08 (m, 2H), 7.30 (d, 2H, J=8.00 Hz); $^{13}$C NMR, trans isomer (125 MHz, CDCl$_3$): δ 24.9, 29.2, 29.6, 29.7, 39.2, 41.5, 47.6, 60.1, 62.9, 117.8, 121.2, 123.8, 124.5, 127.6, 128.8, 130.0, 130.7, 138.1, 143.7, 170.2, 172.2; C NMR, cis isomer (125 MHz, CDCl$_3$): δ 22.6, 29.6, 29.7, 31.6, 39.1, 41.7, 46.9, 60.1, 63.7, 117.8, 121.2, 123.8, 124.7., 127.7, 128.8, 129.9, 130.6, 138.1, 143.7, 170.8, 172.3.

3,3-Dimethylbutyl 2-aminoacetate

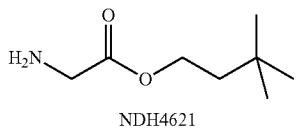

NDH4621

Light yellow liquid, 58% yield; R$_f$ 0.55 (Methylene chloride:methanol, 9:1 with 3 drops NH$_4$OH): $^1$H NMR (500 MHz, CDCl$_3$): δ 0.91 (s, 9H), 1.42-1.47 (bs, 2H), 1.52-1.56 (1, 2H, J=7.50 Hz), 3.38 (s, 2H), 4.13-4.18 (l, 2H, J=7.45 Hz): $^{13}$C NMR (125 MHz, CDCl$_3$): δ 29.7, 29.8, 41.8, 44.1, 62.7, 174.3; HRMS (m/): calc. for C$_8$H$_{17}$NO$_2$ [M+i+]: 160.1332; meas. 160.1321.

3,3-Dimethylbutyl 2-(2-(4-isobutylphenyl)propanamido)acetate

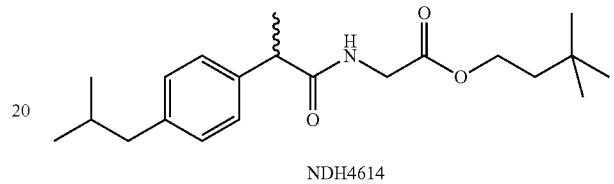

NDH4614

Clear liquid, 91% yield; R$_f$ 0.37 (Hexanes:ethyl acetate 4:1); $^1$H NMR (500 MHz, CDCl$_3$): δ 0.88 (d, 6H, J=6.60 Hz), 0.89 (s, 9H), 1.51 (d, 3H, J=7.15 Hz), 1.49-1.54 (l, 2H, J=5.80 Hz), 1.801.86 (m, 1H), 2.43 (d, 2H, J=7.20 Hz), 3.55-3.60 (q, 1H, J=7.15 Hz), 3.87-4.00 (dq, 2H, J=5.00, 18.5 Hz), 4.12-4.16 (l, 2H, J=7.50 Hz), 5.83 (bs, 1H), 7.10 (d, 2H, J=8.00 Hz), 7.19 (d, 2H, J=8.00 Hz); $^{13}$C NMR (125 MHz, CDCl$_3$): δ 18.4, 22.4, 29.5, 29.7, 30.2, 41.6, 44.9, 45.0, 46.6, 63.2, 127.4, 129.7, 138.1, 140.9, 170.0, 174.6; Calc. for C$_{21}$H$_{33}$NO$_3$.0.25H$_2$O (351.99): C, 71.66; H, 9.59; N, 3.98. Found: C, 71.84; H, 9.35; N, 4.02.

(S)-3,3-Dimethylbutyl 2-(2-(6-methoxynaphthalen-2-yl)propauamido)acetate

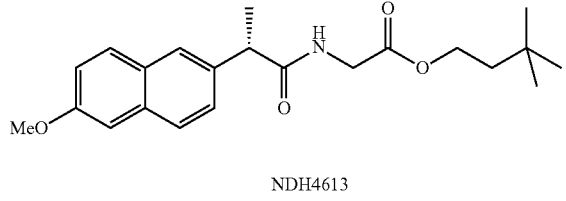 [SMILES: COc1ccc2cc([C@H](C)C(=O)NCC(=O)OCCC(C)(C)C)ccc2c1]

NDH4613

Clear oil, 99% yield; R$_f$ 0.20 (Hexanes:ethyl acetate 4:1); $^1$H NMR (500 MHz, CDCl$_3$): δ 0.87 (s, 9H), 1.45-1.49 (l, 2H, J=7.50 Hz), 1.59 (d, 3H, J=7.20 Hz), 3.71-3.77 (q, 1H, J=7.15 Hz), 3.87-4.00 (dq, 2H, J=5.40, 18.4 Hz), 3.90 (s, 3H), 4.09-4.14 (l, 2H, J=7.40 Hz), 5.85 (bs, 1H), 7.10 (d, 1H, J=2.45 Hz). 7.12-7.15 (dd, 1H, J=2.55, 8.88 Hz), 7.36-7.39 (dd, 1H, J=1.70, 8.43 Hz), 7.67 (s, 1H), 7.68-7.73 (l, 2H, J=8.55 Hz); $^{13}$C NMR (125 MHz, CDCl$_3$): δ 18.4, 29.5, 29.7, 41.6, 41.6, 46.8, 55.3, 63.2, 105.7, 119.2, 126.2, 126.3, 127.6, 129.0, 129.3, 133.8, 136.0, 157.8, 169.9, 174.5; Calc. for C$_{22}$H$_{29}$NO$_4$ (371.47): C, 71.13; H, 7.87; N, 3.77. Found: C, 70.97; H, 7.69; N, 3.80.

3,3-Dimethylbutyl 2-(2-(1-(4-chlorobenzoyl}-5-methoxy-2-methyl-1H-indol-3-yl)acetamnido)acetate

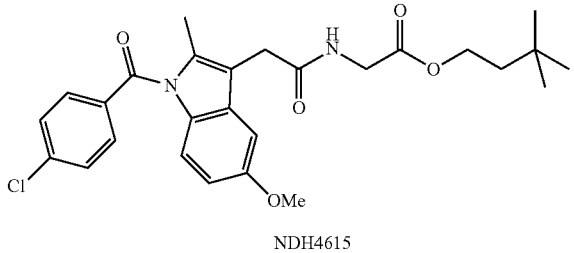 [SMILES: COc1ccc2c(c1)c(CC(=O)NCC(=O)OCCC(C)(C)C)c(C)n2C(=O)c1ccc(Cl)cc1]

NDH4615

Yellow solid, 89% yield; MP 118.5-120° C.; $R_f$ 0.11 (Hexanes:ethyl acetate 4:1); $^1$H NMR (500 MHz, CDCl$_3$): δ 0.89 (s, 9H), 1.48-1.51 (l, 2H, J=7.55 Hz), 2.36 (s, 3H), 3.67 (s, 2H), 3.82 (s, 3H), 3.95 (d, 2H, J=5.40 Hz), 4.11-4.15 (l, 2H, J=7.50 Hz), 6.07-6.09 (l, 1H, J=5.00 Hz), 6.68-6.71 (dd, 1H, J=2.55, 8.95 Hz), 6.91 (s, 1H), 6.90-6.94 (d, 1H, J=1-2 Hz), 7.45-7.48 (m, 2H), 7.64-7.67 (m, 2H); $^{13}$C NMR (125 MHz, CDCl$_3$): δ 13.4, 29.5, 29.7, 32.0, 41.5, 41.6, 55.8, 63.3, 100.8, 112.5, 112.5, 115.1, 129.2, 130.2, 131.0, 131.3, 133.6, 136.4, 139.5, 156.3, 168.3, 169.7, 170.2; Calc. for C$_{27}$H$_{31}$ClN$_2$O$_5$ (499.00): C, 64.99; H, 6.26; N, 5.61. Found: C, 64.63; H, 5.94; N, 5.50.

3,3-Dimethylbutyl 2-(2-(2-(2,6-dichlorophenylamino)phenyl)acetamido)acetate

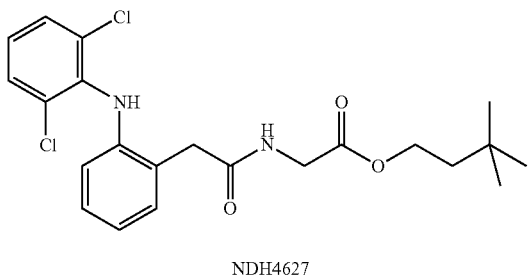 [SMILES: CC(C)(C)CCOC(=O)CNC(=O)Cc1ccccc1Nc1c(Cl)cccc1Cl]

NDH4627

White solid, 70% yield; mp 118-119° C.; $R_f$ 0.36 (Hexanes:ethyl acetate 4:1); $^1$H NMR (500 MHz, CDCl$_3$): δ 0.89 (s, 9H), 1.49-1.53 (l, 2H, J=7.50 Hz), 3.72 (s, 2H), 4.01 (d, 2H, J=5.05 Hz), 4.15-4.18 (l, 2H, J=7.45 Hz), 6.42-6.48 (bs, 1H), 6.49 (d, 1H, J=8.05 Hz), 6.88-6.92 (l, 1H, J=7.40 Hz), 6.93-6.97 (l, 1H, J=8.15 Hz), 7.07-7.11 (l, 1H, J=7.85 Hz), 7.17 (d, 1H, J=7.40 Hz), 7.31 (d, 3H, J=8.10 Hz): $^{13}$C NMR (125 MHz, CDCl$_3$): δ 29.1, 29.2, 40.2, 41.1, 41.3, 62.9, 117.2, 121.2, 123.7, 124.0, 127.6, 128.4, 129.5, 130.2, 137.2, 142.5, 169.4, 171.3; Calc. for C$_{22}$H$_{26}$ClN$_2$O$_3$ (437.36): C, 60.42; H, 5.99: N, 6.41. Found: C, 60.36; H, 6.09; N, 6.26.

(S)-3,3-Dimethylbutyl-2-amino-3-phenylpropanoate

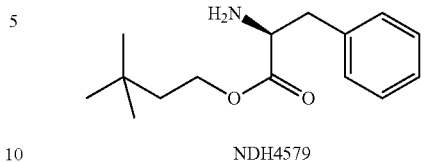

NDH4579

Light yellow liquid, 36% yield; $R_f$ 0.43 (Methylene chloride:hexanes:ethanol, 90:8:2); $^1$H NMR (500 MHz, CDCl$_3$): δ 0.91 (s, 9H), 1.42-1.45 (bs, 2H), 1.49-1.52 (l, 2H, J=7.70 Hz), 2.80-3.08 (dd, 1H, J=7.95, 128 Hz), 2.83-3.06 (dd, 1H, J=7.95, 102 Hz), 3.65-3.70 (dd, 1H, J=5.30, 7.93 Hz), 4.11-4.16 (m, 2H), 7.15-7.19 (d, 2H, J=7.15 Hz), 7.21-7.24 (m, 1H), 7.26-7.30 (m, 2H); $^{13}$C NMR (125 MHz, CDCl$_3$): δ 29.6, 29.7, 41.2, 41.7, 56.0, 62.7, 126.8, 128.6, 129.3, 137.4, 175.1; HRMS (m/z): calc. for C$_{15}$H$_{23}$NO$_2$ 250.1802; meas. 250.1791.

(S)-3,3-Dimethylbutyl 2-(2-(4-isobutylphenyl)propanamido)-3-phenylpropanoate

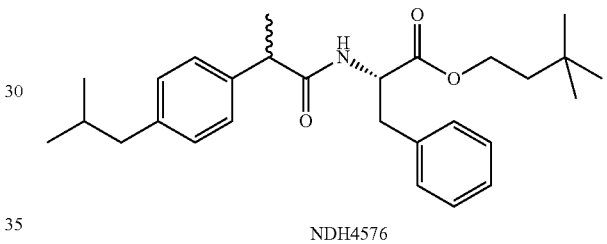

NDH4576

Clear oil, 73% yield; $R_f$ 0.59 (Hexanes:ethyl acetate 4:1); $^1$H N.MR (500 MHz, CDCl$_3$): δ 0.82-1.01 (m, 15H), 1.34-1.53 (m, 5H), 1.78-1.90 (m, 1H), 2.42-2.50 (dd, 2H, J=7.20, 10.9 Hz), 2.94-2.97 (l, 1H, J=3.80 Hz), 2.91-3.07 (m, 1H), 3.44-3.53 (m, 1R), 4.01-4.16 (m, 2H), 4.734.84 (m, 1R), 5.71-5.74 (m, 1R), 6.74 (d, 1H, J=7.20 Hz), 6.90-6.93 (m, 1R), 7.05-7.16 (m, 5R), 7.15-7.20 (m, 2R); $^{13}$C NMR (125 MHz, CDCl$_3$): δ 18.19, 22.42, 29.52, 29.53, 29.65, 29.69, 30.20, 30.24, 37.72, 37.76, 41.55, 41.60, 45.06, 45.08, 46.62, 46.72, 52.92, 53.15, 63.16, 63.20, 126.89, 126.96, 127.40, 127.41, 128.37, 128.45, 129.24, 129.29, 129.60, 129.62, 135.63, 135.85, 137.67, 138.27, 140.74, 171.40, 171.49, 173.59, 173.96: Calc. for C$_{25}$H$_{39}$NO$_3$ (437.61): C, 76.85; H, 8.98; N, 3.20. Found: C, 76.90: H, 9.19; N, 3.17.

(S)-3,3-Dimethylbutyl 2-((S)-2-(6-methoxynaphthalen-2-yl)propanamido)-3-phenylpropanoate

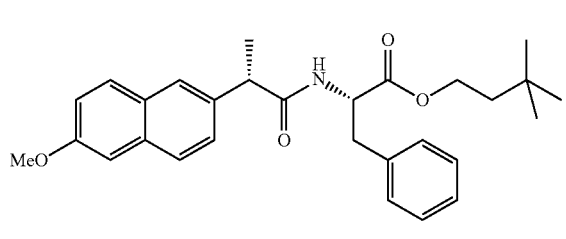

NDH4572

Clear oil, 82% yield; $R_f$ 0.42 (Hexanes:ethyl acetate 4:1): $^1$H N.MR (500 MHz, CDCl$_3$): δ 0.83 (s, 9R), 1.36-1.40 (l, 2H, J=7.45 Hz), 1.57 (d, 3H, J=7.25 Hz), 2.94-3.05 (dq, 2H, J=5.75, 13.8 Hz), 3.65-3.70 (q, 1H, J=7.20 Hz), 3.91 (s, 3R), 3.99-4.10 (m, 2R), 4.73-4.78 (m, 1R), 5.78 (d, 1H, J=7.75 Hz), 6.83-6.86 (m, 2H), 7.02-7.06 (l, 2H, J=7.65 Hz), 7.09-7.15 (m, 3R), 7.29-7.32 (dd, 1H, J=1.80, 8.50 Hz), 7.58 (s, 1R), 7.66 (dd, 2H, J=4.05, 8.68 Hz); $^{13}$C NMR (125 MHz, CDCl$_3$): δ 18.1, 29.5, 29.6, 37.7, 41.5, 47.0, 53.1, 55.4, 63.2, 105.6, 119.1, 126.2, 126.4, 126.9, 127.5, 128.4, 129.0, 129.2, 129.3, 133.8, 135.6, 135.7, 157.8., 171.3, 173.9; Calc. for C$_{29}$H$_{35}$NO$_4$ (461.59): C, 75.46; H, 7.64: N, 3.03. Found: C, 75.03: H, 7.59; N, 3.03.

(S)-3,3-Dimethylbutyl 2-(2-(1-(4-chlorobenzoyl)-5-methoxy-2-methyl-1H-indol-3-yl)acetamido)3-phenylpropanoate

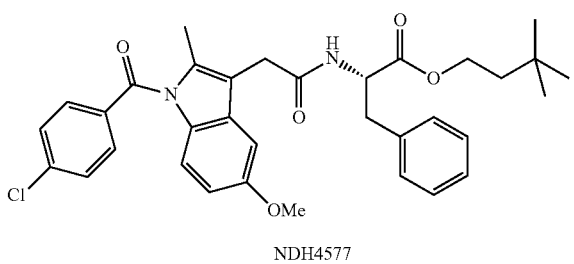 [SMILES: COc1ccc2c(c1)c(CC(=O)N[C@@H](Cc1ccccc1)C(=O)OCCC(C)(C)C)c(C)n2C(=O)c1ccc(Cl)cc1]

NDH4577

Light yellow oil, 92% yield; $R_f$ 0.21 (Hexanes:ethyl acetate 4:1); $^1$H NMR (500 MHz, CDCl$_3$): δ 0.87 (s, 9R), 1.43-1.49 (l, 2H, J=7.50 Hz), 2.19 (s, 3R), 2.94-3.03 (m, 2H), 3.55-3.63 (q, 2H, J=17.5, 18.6 Hz), 3.80 (s, 3R), 4.06-4.15 (n 2R), 4.78-4.82 (m, 1R), 5.97 (d, 1H, J=8.05 Hz), 6.72-6.75 (dd, 1H, J=2.55, 9.03 Hz), 6.77 (d, 2H, J=7.15 Hz), 6.86 (d, 1H, J=2.45 Hz), 6.997.03 (m, 3R), 7.06-7.12 (m, 1R), 7.42 (d, 2H, J=8.75 Hz), 7.53 (d, 2H, J=7.75 Hz); $^{13}$C NMR (125 MHz, CDCl$_3$): δ 13.3, 29.5, 29.7, 32.1, 37.6, 41.6, 52.9, 55.8, 63.3, 100.7, 112.5, 112.6, 115.2, 127.0, 128.4, 129.1, 129.2, 130.2, 131.0, 131.2, 133.7, 135.4, 136.0, 139.4, 156.4, 168.2, 169.3, 171.1; Calc. for C$_{34}$H$_{37}$ClN$_2$O$_5$ (589.12): C. 69.32; H. 6.33; N, 4.76. Found: C, 68.85; H, 6.13; N, 4.60.

(S)-3,3-Dimethylbutyl 2-(2-(2-(2,6-dichlorophenylamino)phenyl)acetamido)-3-phenylpropanoate

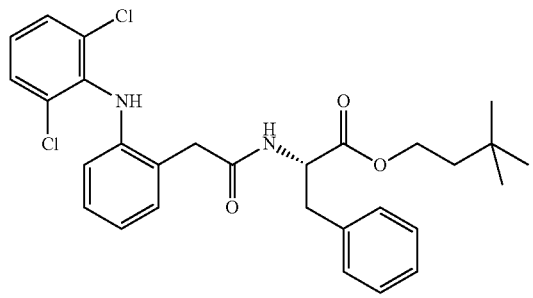

NDH4578

Light yellow oil, 92% yield; $R_f$ 0.65 (Hexanes:ethyl acetate 4:1); $^1$H NMR (500 MHz, CDCl$_3$): δ 0.89 (s, 9H), 1.45-1.50 (m, 2H), 3.04-3.13 (m, 2H), 3.59-3.72 (q, 2H, J=14.4, 45.4 Hz), 4.064.18 (m, 2H), 4.83-4.87. (m, 1H), 6.13 (d, 1H, J=7.80 Hz), 6.50 (d, 1H, J=7.90 Hz), 6.89-6.98 (m, 3H), 6.95-6.98 (l, 1H, J=8.00 Hz), 7.10 (d, 2H, J=7.40 Hz), 7.16-7.19 (m, 3H), 7.32 (d, 2H, J=8.05 Hz). 7.36 (bs, 1H); $^{13}$C NMR (125 MHz, CDCl$_3$): δ 29.5, 29.7, 37.7, 41.0, 41.6, 53.3, 63.4, 117.7, 121.6, 124.2, 124.4, 127.1, 128.0, 128.5, 128.8, 129.4, 130.1, 130.6, 135.6, 137.7, 143.0, 170.9, 171.3; Calc. for C$_{29}$H$_{32}$Cl$_2$N$_2$O$_3$.0.5H$_2$O (536.49): C, 64.92; H, 6.20; N, 5.22. Found: C, 64.99; H, 5.78; N, 5.05.

(S)-3,3-Dimethylbutyl 2-amino-3-methylbutanoate

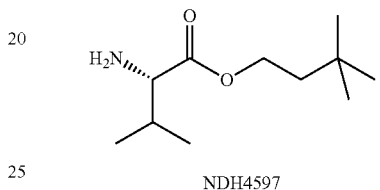

NDH4597

Light yellow liquid, 64% yield; $R_f$ 0.16 (hexanes:ethyl acetate: 4:1); $^1$H NMR (500 MHz, CDCl$_3$): δ 0.87 (d, 3H, J=6.85 Hz), 0.92 (s, 9H), 0.95 (d, 3H, J=6.90 Hz), 1.38-1.45 (bs, 2H), 1.53-1.57 (l, 2H, J=7.70 Hz), 1.97-2.02 (m, 1H), 3.23 (d, 1H, J=4.95 Hz). 4.13-4.16 (l, 2H, J=7.35 Hz); $^{13}$C NMR (125 MHz, CDCl$_3$): δ 17.2, 19.4, 29.6, 29.7, 32.1, 41.8, 60.0, 62.5, 175.7; HRMS (m/z): calc. for C$_{11}$H$_{23}$NO$_2$ 202.1802; meas. 202.1784.

(S)-3,3-Dimethylbutyl 2-(2-(4-isobutylphenyl)propanamido)-3-methylbutanoate

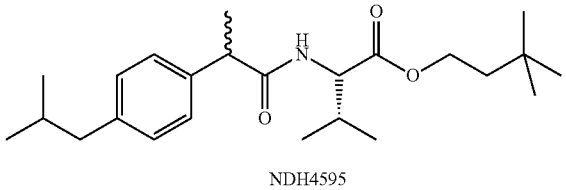

NDH4595

Clear liquid, 92% yield; $R_f$ 0.55 (Hexanes:ethyl acetate 4:1); $^1$H NMR (500 MHz, CDCl$_3$): δ 0.64(d, 1.5H, J=6.90 Hz), 0.71-0.75 (dd, 3H, J=6.85, 9.20 Hz). 0.83 (d, 1.5H, J=6.85 Hz), 0.85-0.87 (m, 6H), 0.89 (s, 4.5H), 0.90 (s, 4.5H), 1.46-1.53 (m, 5H), 1.79-1.86 (m, 1H), 1.99-2.10 (m, 1H), 2.43 (d, 2H, J=7.20 Hz), 3.53-3.57 (q, 0.5H, J=7.15 Hz), 3.57-3.62 (q, 0.5H, J=7.30 Hz), 4.07-4.14 (m, 2H), 4.43-4.49 (m, 1H), 5.70-5.78 (dd, 1H, J=8.80, 24.8 Hz), 7.09-7.12 (m, 2H), 7.17-7.22 (m, 2H); $^{13}$C NMR. (125 MHz, CDCl$_3$): 0 17.3, 17.5, 18.1, 18.3, 18.9, 19.0, 22.2, 22.3, 29.5, 29.6, 29.7, 30.2, 31.2, 31.3, 41.6, 41.7, 45.0, 45.1, 46.8, 46.9, 56.8, 56.9, 62.9, 63.0, 127.3, 127.4, 129.7, 138.6, 140.8, 140.9, 171.9, 172.1, 174.1, 174.4; Calc. for C$_{24}$H$_{39}$NO$_3$ (389.57): C, 73.99; H, 10.09; N, 3.60. Found: C, 73.90; H, 10.50; N, 3.52.

(S)-3,3-Dimethylbutyl 2-((S)-2-(6-methoxynaphthalen-2-yl)propanamido)-3-methylbutanoate

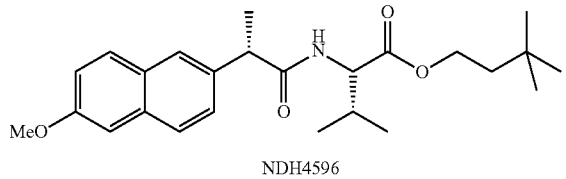

NDH4596

Clear oil, 99% yield; R$_f$ 0.30 (Hexanes:ethyl acetate 4:1); H NMR (500 MHz, CDCl$_3$): δ 0.73 (d, 3H, J=6.90 Hz), 0:84 (s, 9H), 0.85 (d, 3H, J=7.00 Hz), 1.38-1.42 (l, 2H, J=7.65 Hz), 1.54 (s, 3H), 1.60 (d, 3H, J=7.20 Hz), 2.05-2.10 (m, 1H), 3.71-3.77 (n, 1H), 3.90 (s, 3H), 4.02-4.06 (l, 2H, J=7.45 Hz), 4.46-4.49 (dd, 1H, J=4.75, 8.73 Hz), 7.09-7.14 (m, 2H), 7.36-7.40 (dd, 1H, J=1.65, 8.48 Hz), 7.68 (s, 1H), 7.69-7.72 (dd, 2H, J=5.50, 8.60 Hz); $^{13}$C NMR (125: MHz, CDCl$_3$): δ 17.7, 18.5, 19.0, 20.8, 29.5, 29.6, 31.3, 41.6, 47.1, 55.3, 57.1, 62.9, 105.7, 119.1, 126.2, 126.4, 127.5, 129.0, 129.3, 133.8, 135.9, 157.7, 174.2, 186.2; Calc. for C$_{25}$H$_{35}$NO$_4$ (413.55): C, 72.61; H, 8.53; N, 3.39. Found: C. 72.62; H, 8.87; N. 3.29.

(S)-3,3-Dimethylbutyl 2-(2-(1-(4-chlorobenzoyl)-5-methoxy-2-methyl-1H-indol-3-yl)acetamido)3-methylbutanoate

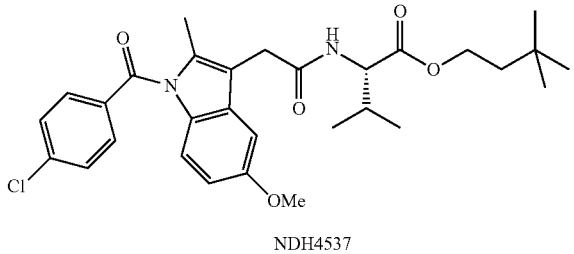 [SMILES: COc1ccc2c(c1)c(CC(=O)N[C@H](C(=O)OCCC(C)(C)C)C(C)C)c(C)n2C(=O)c1ccc(Cl)cc1]

NDH4537

White solid, 93% yield; mp 119-120° C., R$_f$ 0.16 (Hexanes:ethyl acetate 4:1): $^1$H NMR (500 MHz, CDCl$_3$): δ 0.69 (d, 3H, J=6.90 Hz), 0.83 (d, 3H, J=6.85 Hz), 0.88 (s, 9H), 1.44-1.48 (l, 2H, J=7.55 Hz), 2.05-2.10 (m, 1H), 2.35 (s, 3H), 3.65 (m, 2H), 3.80 (s, 3H), 4.08-4.11 (l, 2H, J=7.50 Hz), 4.48-4.52 (dd, 1H, J=4.75, 8.83 Hz), 6.07 (d, 1H, J=8.80 Hz), 6.68-6.71 (dd, 1H, J=2.50, 9.00 Hz), 6.89 (d, 1H, J=2.45 Hz), 6.94 (d, 1H, J=9.00 Hz), 7.44-7.48 (m, 2H), 7.63-7.66 (m, 2H); $^{13}$C NMR (125 MHz, CDCl$_3$): δ 13.4, 17.6, 19.0, 29.5, 29.7, 31.2, 32.3, 41.6, 55.7, 57.1, 63.1, 100.6, 100.9, 112.6, 112.7, 115.2, 129.2, 130.2, 131.0, 131.2, 133.7, 136.2, 139.5, 156.3, 169.7, 171.7; Calc. for C$_{30}$H$_{37}$ClN$_2$O$_5$ (541.08): C, 66.59; H, 6.89; N, 5.18. Found: C. 66.48; H. 7.12; N, 5.10.

(S)-3,3-Dimethylbutyl 2-(2-(2-(2,6-dichlorophenylamino)phenyl)acetamido)-3-methylbutanoate

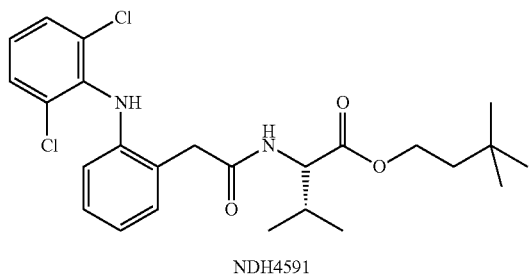

NDH4591

Clear oil, 100% yield; R$_f$ 0.54 (Hexanes:ethyl acetate 4:1); $^1$H NMR (500 MHz, CDCl$_3$): δ 0.85 (d, 3H, J=6.90 Hz), 0.88 (d, 3H, J=6.85 Hz), 0.90 (s, 9H), 1.49-1.53 (l, 2H, J=7.55 Hz), 2.11-2.15 (m, 1H), 3.72 (s, 2H), 4.12-4.16 (m, 2H), 4.53-4.57 (dd, 1H, J=4.90, 8.83 Hz), 6.16 (d, 1H, J=8.90 Hz), 6.50 (d, 1H, J=7.95 Hz), 6.89-6.92 (td, 1H, J=0.95, 7.45 Hz), 6.93-6.97 (l, 1H, J=8.00 Hz), 7.07-7.11 (td, 1H, J=1.55, 9.18 Hz), 7.16-7.19 (dd, 1H, J=1.35, 7.50 Hz), 7.31 (d, 2H, J=8.05 Hz), 7.36 (s, 1H); $^{13}$C NMR (125 MHz, CDCl$_3$): 0 17.8, 18.9, 29.6, 29.7, 31.4, 41.0, 41.7, 57.2, 63.1, 117.8, 121.6, 124.1, 124.8, 128.0, 128.8, 129.9, 130.5, 137.8, 143.0, 171.4, 171.9; Calc. for C$_{25}$H$_{32}$Cl$_2$N$_2$O$_3$ (479.44): C, 62.63; H, 6.73; N. 5.84. Found: C, 62.46: H, 6.48; N, 5.66.

TABLE II

Representative amino acid anti-inflammatory conjugates of Aspect II prepared by methods indicated herein are shown as examples, without limitation, of the compositions claimed herein.

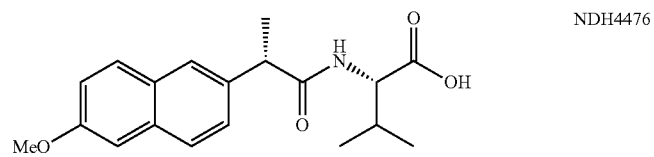

NDH4476

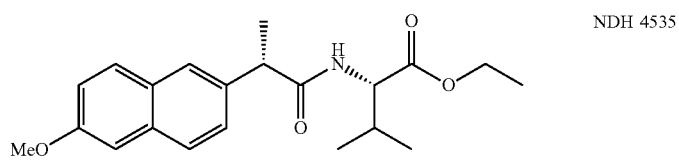

NDH 4535

TABLE II-continued
Representative amino acid anti-inflammatory conjugates of Aspect II prepared by methods indicated herein are shown as examples, without limitation, of the compositions claimed herein.
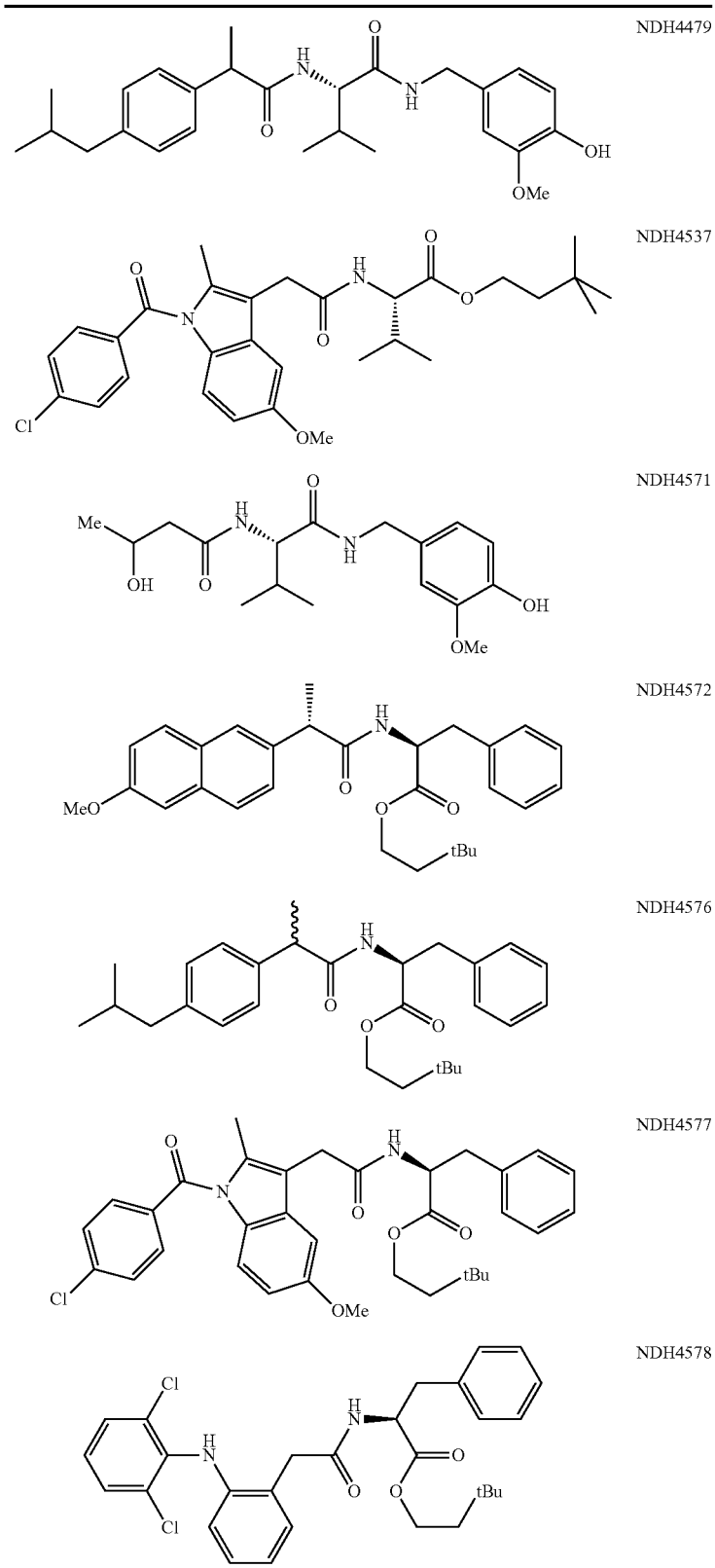

TABLE II-continued
Representative amino acid anti-inflammatory conjugates of Aspect II prepared by methods indicated herein are shown as examples, without limitation, of the compositions claimed herein.
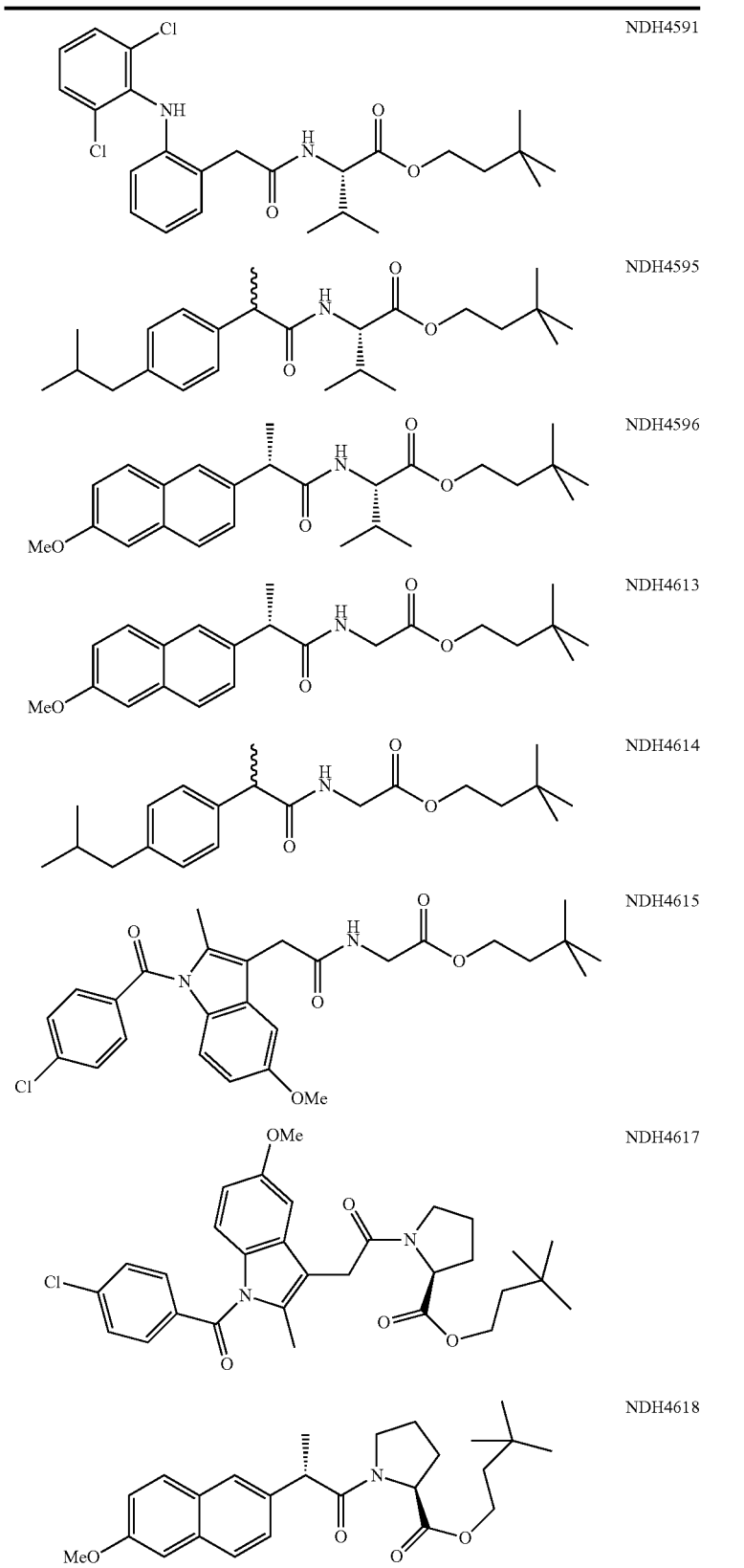

TABLE II-continued
Representative amino acid anti-inflammatory conjugates of Aspect II prepared by methods indicated herein are shown as examples, without limitation, of the compositions claimed herein.
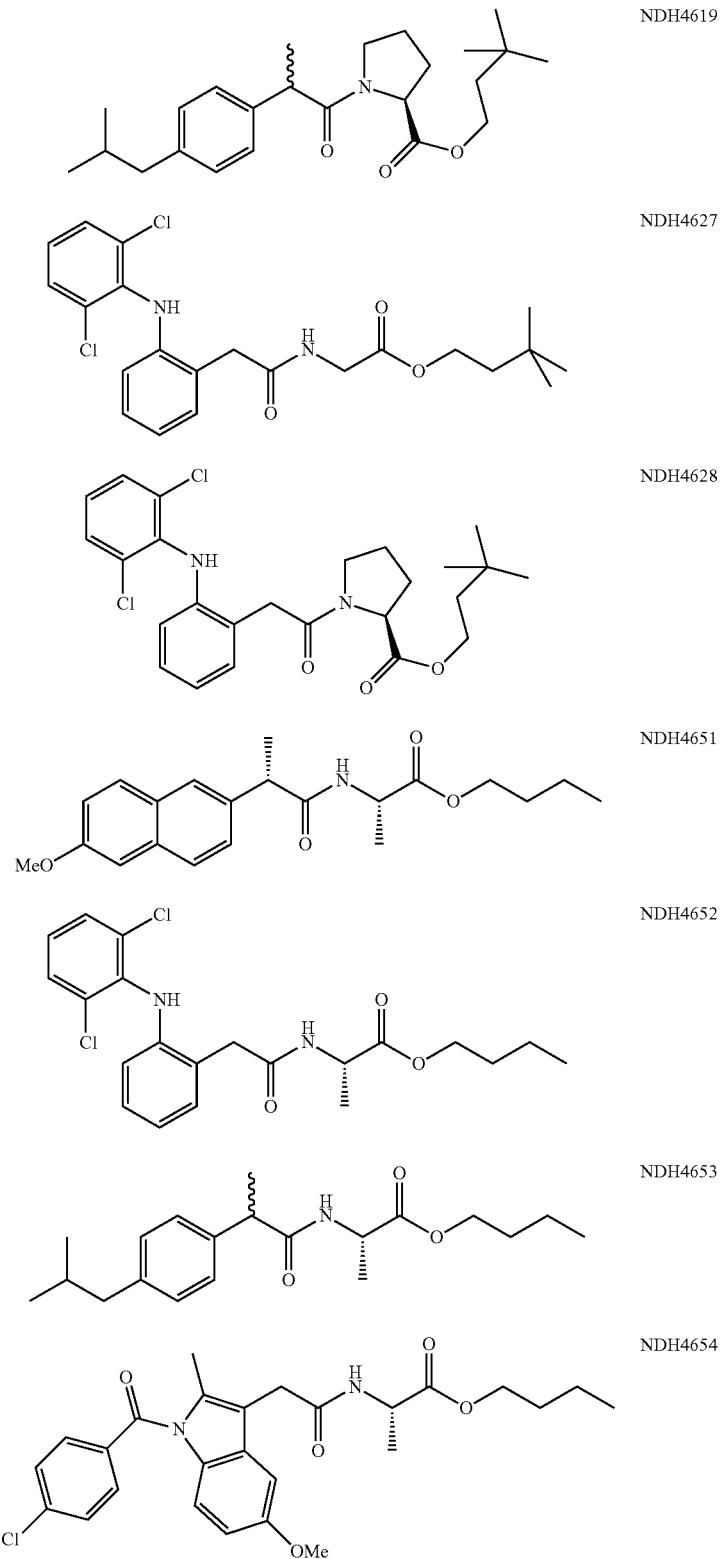
NDH4619
NDH4627
NDH4628
NDH4651
NDH4652
NDH4653
NDH4654

TABLE II-continued

Representative amino acid anti-inflammatory conjugates of Aspect II prepared by methods indicated herein are shown as examples, without limitation, of the compositions claimed herein.

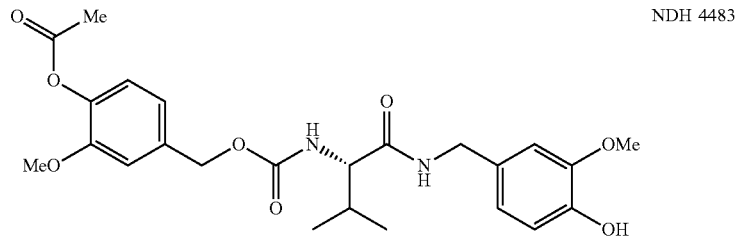

NDH 4483

All references cited herein are incorporated herein by reference in their entireties.

What is claimed is:

1. An anti-inflammatory conjugate having the structure of:

vanilloid-(carbamate)-polyamine-(carbamate)-vanilloid, or      Formula 2A, terpene-(carbamate)-polyamine-(carbamate)-terpene,      Formula 4A, wherein said terpenes of Formula 4A, are independently selected from the group consisting of thymol, carvacrol, menthol, geraniol, nerol, farnesol and perillyl alcohol;

wherein said polyamine of Formula 2A and 4A is selected from the group consisting of putrescine, spermidine and spermine; and wherein said vanilloids of Formula 2A, are independently selected from the group consisting of zingerone, eugenol, vanillyl alcohol, 3-methoxy-4-acetyloxybenzyl alcohol, and vanillylamine.

2. The conjugate of claim 1, Formula 4A, wherein said terpenes are the same terpene.

3. The conjugate of claim 1, Formula 4A, wherein said terpenes are different terpenes.

4. The conjugate of claim 1, Formula 2A, wherein said vanilloids are the same vanilloid.

5. The conjugate of claim 1, Formula 2A, wherein said vanilloids are different vanilloids.

6. A method of increasing the potency of an anti-inflammatory compound, comprising conjugating said anti-inflammatory compound with another anti-inflammatory compound via a carbamate linkage to produce a conjugate, wherein the structure of the conjugate is selected from the group consisting of Formulae 2A and 4A:

vanilloid-(carbamate)-polyamine-(carbamate)-vanilloid, or      Formula 2A, terpene-(carbamate)-polyamine-(carbamate)-terpene,      Formula 4A, wherein said terpenes of Formula 4A, are independently selected from the group consisting of thymol, carvacrol, menthol, geraniol, nerol, farnesol and perillyl alcohol;

wherein said polyamine of Formula 2A and 4A is selected from the group consisting of putrescine, spermidine and spermine; and wherein said vanilloids of Formula 2A, are independently selected from the group consisting of zingerone, eugenol, vanillyl alcohol, 3-methoxy-4-acetyloxybenzyl alcohol, and vanillylamine.

7. The method of claim 6, comprising two terpenes which are the same.

8. The method of claim 6, comprising two terpenes which are different.

9. The method of claim 6, comprising two vanilloids which are the same.

10. The method of claim 6, comprising two vanilloids which are different.

* * * * *